US007612168B2

(12) United States Patent
Sorensen

(10) Patent No.: US 7,612,168 B2
(45) **Date of Patent: *Nov. 3, 2009**

(54) MODIFIED HIV PEPTIDES, ANTIGENS, COMPOSITIONS, IMMUNOASSAY KIT AND A METHOD OF DETECTING ANTIBODIES INDUCED BY HIV

(75) Inventor: Birger Sorensen, Skien (NO)

(73) Assignee: Bionor Immuno As, Gulset Skien (NO)

( * ) Notice: Subject to any disclaimer, the term of this patent is extended or adjusted under 35 U.S.C. 154(b) by 167 days.

This patent is subject to a terminal disclaimer.

(21) Appl. No.: 11/211,576

(22) Filed: Aug. 26, 2005

(65) Prior Publication Data

US 2007/0237783 A1 Oct. 11, 2007

Related U.S. Application Data

(62) Division of application No. 10/129,331, filed as application No. PCT/NO01/00362 on Sep. 3, 2001, now Pat. No. 7,009,037.

(30) Foreign Application Priority Data

Sep. 4, 2000 (NO) ................................ 2000-4413

(51) Int. Cl.
*C07K 1/00* (2006.01)

(52) U.S. Cl. ................. 530/350; 424/185.1; 424/188.1; 424/208.1; 530/324; 530/325; 530/326; 530/327; 530/328; 530/329

(58) Field of Classification Search ....................... None
See application file for complete search history.

(56) References Cited

U.S. PATENT DOCUMENTS

| | | | |
|---|---|---|---|
| 5,972,339 | A | 10/1999 | Walker |
| 6,706,859 | B1 | 3/2004 | Sorensen |

FOREIGN PATENT DOCUMENTS

| | | |
|---|---|---|
| EP | 0732339 | 9/1996 |
| GB | 2236754 | 4/1991 |
| WO | 9837089 | 8/1989 |
| WO | 91/13360 | 9/1991 |
| WO | 92/22572 | 12/1992 |
| WO | 98/29551 | 7/1998 |
| WO | 9958658 | 11/1999 |
| WO | 00/52040 | 9/2000 |

OTHER PUBLICATIONS

Phillips, et al., "Human immunodeficiency virus genetic variation that can escape cytotoxic T cell recognition," Nature, vol. 354, Dec. 1991, pp. 453-459.

Klenerman, et al., "Cytotoxic T-cell activity antagonized by naturally occurring HIV-1 Gag variants," Nature, vol. 369, No. 6479, Jun. 1994, pp. 403-407.

Goulder, et al., "Differential Narrow Focusing of Immunodominant Human Immunodeficiency Virus Gag-Specific Cytotoxic T-Lymphocyte Responses in Infected African and Caucasoid Adults and Children," Journal of Virology, vol. 74, No. 12, Jun. 2000, pp. 5679-5690.

Mathiesen, et al., "Mapping of IgG subclass and T-cell epitopes on HIV proteins by synthetic peptides," Immunology, vol. 67, No. 4, 1989, pp. 453-459.

Truong et al., "Comparison of antibody responses to different forms of HIV-1 core antigens by epitope mapping", *J. Medical Virology*, vol. 51, pp. 145-151, 1997.

Chong et al. *Int. J. Peptide Protein Res.*, vol. 41, pp. 21-27, 1992.

Ruan et al., "The Drosophila Insulin Receptor Contains a Novel Carboxyl-terminal Extension Likely to Play an Important Role in Signal Transduction", *Journal of Biological Chemistry*, vol. 270, No. 9, pp. 4236-4243, 1995.

Riffkin et al., AA single amino-acid change between the antigenically different extracellular serine proteases V2 and B2 from Dichelobacter nodosus@, *Gene*, vol. 167, pp. 279-283, 1995.

Abaza et al., A Effects of amino acid substitutions outside an antigenic site on protein binding to monoclonal antibodies of predetermined specificity obtained by peptide immunization@, *Journal of Protein Chemistry*, vol. 11, No. 5, pp. 433-444, 1992.

Cruse et al., *Illustrated Dictionary of Immunology*, (Boca Raton, FL, CRC Press, Inc., 1995), p. 309. QR180.4.C78.

Paul, *Fundamental Immunology*, (Philadelphia & New York, Lippincott-Raven Publishers, 1993), pp. 250 and pp. 1311-1312. QR181. F84.

Cohen et al., A Pronounced acute immunosuppression in vivo medicated by HIV Tat challenge@, *Proceedings of the National Academy of Sciences of the United States of America*, vol. 96, Issue 19, pp. 10842-10847, 1999.

*Primary Examiner*—Jeffrey S. Parkin
*Assistant Examiner*—Louise Humphrey
(74) *Attorney, Agent, or Firm*—Wenderoth, Lind & Ponack, L.L.P.

(57) ABSTRACT

The present invention comprises novel and modified peptides capable of inducing a HIV-1 specific immune response without antagonizing the cytotoxic T-cell activity in order to achieve an effective prophylactic and therapeutic vaccine against HIV. The peptides are based on conserved regions of HIV gag p17 and p24 proteins. Antigens in free- or carrier-bound form comprising at least one of the said peptides, vaccine compositions containing at least one of the antigens, immunoassay kits and a method of detecting antibodies induced by HIV or HIV specific peptides using such antigens, are described.

15 Claims, No Drawings

MODIFIED HIV PEPTIDES, ANTIGENS, COMPOSITIONS, IMMUNOASSAY KIT AND A METHOD OF DETECTING ANTIBODIES INDUCED BY HIV

This application is a divisional application of application Ser. No. 10/129,331, filed Jun. 11, 2002, now U.S. Pat. No. 7,009,037, which is a 371 National Stage Application of PCT/NO01/00362, filed Sep. 3, 2001.

The present invention relates to novel peptides based on conserved regions of HIV gag p17 and p24, antigens in free or carrier-bound form comprising at least one of the said peptides, vaccine compositions containing at least one of the antigens, immunoassay kits and a method of detecting antibodies, induced by human immunodeficiency virus (HIV) or HIV-specific peptides, using such antigens.

BACKGROUND

There is an urgent need to control the global epidemic of HIV infection and the development of a vaccine against HIV is one of the major objectives in AIDS research. In general vaccines should activate antigen presenting cells, overcome genetic restriction in T-cell responses and generate T- and B-memory cells. The variability of the viral population poses a further difficulty in obtaining an effective HIV vaccine. A break through in the ongoing attempts to develop a vaccine against AIDS has so far not been reported. It is now generally accepted that an induction of antigen-specific humoral and cell-mediated immunity is crucial for a development of an effective prophylactic and therapeutic vaccine. All three arms of the immune system including neutralizing antibodies; CD8+CTL and T-helper-1 (TH1) cells might be required for protective immunity to HIV. It is known that CTL can clear other viral infections (Ada, Immunol. Cell Biol., 72:447-454, 1994) and that CTL can lyse infected targets early in infection before viral progeny can be produced and released by cell lysis, Ada et al., supra. The focus has been on selection of antigens as well as on design and evaluation of different adjuvances. The antigens used in different in vitro and in vivo studies have been all from crude proteins to various synthetic peptides from several of the HIV proteins. A large number of studies have been done on the V3 loop of gp120. Induction of both B- and T-cell responses have been observed, however, it has been reported from an in vitro study that a peptide from the conserved region of gp41 have indicated infection enhancement (Bell S. J., et al., Clin. Exp. Immunol., 87 (1): 37-45, (January 1992).

Naturally occurring HIV sequences in vaccine candidates are not capable of stimulating a stable immune response due to the viruses inherent ability to hide by changing the appearance of the epitopes presented on the cell surface of infected cells. The immune system is fooled to believe that a particular amino acid sequence is relevant when in fact the amino acids of importance is hidden.

A recent study of titers of antibodies against the gag p24 protein, has shown that slow progression towards development of AIDS is associated with high titers, while fast progression towards development of AIDS is associated with low titers. It is shown that persons with low p24 antibody titer develop significantly faster AIDS than persons with high p24 antibody titers (Zwart G., et al. Virology, 201, p. 285-93, June 1994), indicating that gag and p24 in particular can play a key role to control the development of AIDS.

New HIV p24 peptides are described in WO91/13360, wherein the peptides are used in a method of discriminating between a false and true diagnosed HIV-positive serum sample.

Johnson R. P., et al., The Journal of Immunology, Vol. 147, p. 1512-1521, No. 5, Sep. 1, 1991 describe an analysis of the fine specificity of gag-specific CTL-responses in three HIV-1 seropositive individuals, the gag-specific CTL-responses were found to be mediated by CD3+ CD8+ lymphocytes which are HLA class I restricted. Goulder P. J. R. et. al., Journal of Virology, Vol. 74, p. 5679-5690, No 12, June 2000 has studied CTL response from different parts of p17 and p24 of HIV in different populations. The findings show that certain immunodominant regions exist, however, minor differences in amino acid composition can cause large differences in response.

EP-A-0 356 007 discloses antigenic determinants, in particular it relates to synthetic polypeptide sequences which are related to proteins present in the HIV-1 and which can be used as a basis for a potential vaccine against AIDS.

Rosenberg E. S. et al., Science, Vol. 278, 21 Nov. 1997, p. 1447-1450 describe that virus specific CD4+ T helper lymphocytes are critical to the maintenance of effective immunity in a number of chronic viral infections, but are characteristically undetectable in chronic human immunodeficiency virus-type 1 (HIV-1) infection. HIV-1-specific proliferative responses to p24 were inversely related to viral load. They conclude that the HIV-1-specific helper cells are likely to be important in immunotherapeutic interventions and vaccine development.

EP 0 230 222, EP 0 270 114, DE 37 11 016 and GB 2 188 639 all in the name of F. Hoffmann-La Roche & Co. Aktiengesellschaft concern recombinant expression and purification of an HTLVIII Gag/Env gene protein or fusion proteins. The proteins consisting of native sequences can be purified to homogeneity and used as a basis for diagnostic tests for detection of antibodies against viruses associated with AIDS. The gag/env protein may also be formulated for use as a vaccine for protection against AIDS through prophylactic immunization.

From a diagnostic and therapeutic point of view, the major problems with using p24 as part of an assay or therapy is associated with the high number of epitopes on p24 which stimulates production of a large number of antibodies with poor specificity, which through repeated boostering on potential mutated sequences can create autoantibodies (Autoantibodies to the alfa/beta T-cell receptors in HIV infection; dysregulation and mimicry. Lake D. F., et al., Proc. Natl. Acad. Sci. USA, (23): 10849-53, Nov. 8, 1994). Further, it is reported that the p24 antibody titer does not reach the same high levels as for the envelope proteins (gp120 and gp41). Normally antibodies to p24 are developed in the very early phase of the infection, but the titer is fairly quickly stabilized after the initial infection period. Later the p24 titer is gradually decreasing while the opposite happens with gp160. These findings can also be seen in relation to recent reports stating that cytotoxic T-cell activity is antagonized by naturally occurring HIV-1 gag variants (Klenerman P., et al., Nature, 2:369 (6479), p. 355, 2 Jun. 1994). This can be one of the reasons why a rapid stabilization of the p24 titer is seen and why it later starts to decrease.

Based on the above background data, we decided to investigate the possibility of designing novel synthetic peptides which can mimic the p17 and p24 epitopes without antagonizing the cytotoxic T-cell activity, in order to meet the need for an effective prophylactic and therapeutic vaccine.

The sequence of p17 identified as a possible template for development of peptides that can elicit CTL and antibody response is published by Korber B., et al., Human Retroviruses and AIDS 1999 Eds. Theoretical Biology and Biophysics Group, Los Alamos National Laboratory, Los Alamos, N. Mex. The identified amino acid sequence is located between the amino acids 33 and 53, confer table 1:

TABLE 1

| AA no. | AA sequence | Naturally occurring AA's | | | | |
|---|---|---|---|---|---|---|
| 33 | H | | | | | |
| 34 | I | L | V | M | | |
| 35 | I | V | | | | |
| 36 | W | | | | | |
| 37 | A | | | | | |
| 38 | S | N | R | | | |
| 39 | R | S | | | | |
| 40 | E | | | | | |
| 41 | L | M | | | | |
| 42 | E | D | K | G | Q | |
| 43 | R | K | G | N | | |
| 44 | F | S | Y | | | |
| 45 | A | T | S | | | |
| 46 | V | L | I | C | | |
| 47 | N | D | S | | | |
| 48 | P | R | S | T | | |
| 49 | G | S | A | D | N | Q |
| 50 | L | F | | | | |
| 51 | L | M | | | | |
| 52 | E | G | D | | | |
| 53 | T | S | A | | | |

The one letter as well as the three letter codes defining the amino acids in the sequences give throughout this specification are in accordance with International standards and given in textbooks, for instance Lehninger A. L., <<(Principles of Biochemistry>>, Worth Publishers Inc., New York, 1982. The amino acids given to the right of the second column represent the natural variation of the sequence. A change in the overall charge of the epitope by modification of amino acids can involve a significant improvement of the immunogenicity. The modifications involve a probable conformation change from the original helical to a sheet structure, exposing the epitope to the immune system in a different manner and expectingly to a greater extent.

To further increase the number of T-cell epitopes and reduce the probability for development of escape mutants within the gag protein three additional peptide sequences from p24 were based on the following three sequences from residues 133-158, 178-199 and 233-251, respectively published in Human Retroviruses and AIDS 1999; A Compilation and Analysis of Nucleic Acid and Amino Acid Sequences. Eds. Theoretical Biology and Biophysics Group, Los Alamos National Laboratory, Los Alamos, confer tables 2-4:

TABLE 2

| AA no. | AA sequence | Naturally occurring AA's at each AA position | | | |
|---|---|---|---|---|---|
| 133 | P | | | | |
| 134 | I | V | L | | |
| 135 | V | M | A | I | |
| 136 | Q | S | T | V | |
| 137 | N | D | T | | |
| 138 | I | A | L | M | |
| 139 | Q | E | K | G | |
| 140 | G | | | | |
| 141 | Q | I | | | |
| 142 | M | P | A | | |
| 143 | V | I | A | T | R |
| 144 | H | | | | |
| 145 | Q | H | | | |
| 146 | A | S | V | N | P |
| 147 | I | L | M | V | |
| 148 | S | T | | | |
| 149 | P | A | | | |
| 150 | R | | | | |
| 151 | T | | | | |
| 152 | L | S | | | |
| 153 | N | F | | | |
| 154 | A | | | | |
| 155 | W | | | | |
| 156 | V | | | | |
| 157 | K | | | | |
| 158 | V | A | C | | |

TABLE 3

| AA no. | AA sequence | Naturally occurring AA's at each AA position | | | | |
|---|---|---|---|---|---|---|
| 178 | G | | | | | |
| 179 | A | | | | | |
| 180 | T | A | I | V | L | |
| 181 | P | S | | | | |
| 182 | Q | H | G | T | S | Y |
| 183 | D | | | | | |
| 184 | L | I | V | | | |
| 185 | N | Y | | | | |
| 186 | T | M | L | A | | |
| 187 | M | | | | | |
| 188 | L | | | | | |
| 189 | N | S | T | | | |
| 190 | T | I | V | A | | |
| 191 | V | I | | | | |
| 192 | G | | | | | |
| 193 | G | D | | | | |
| 194 | H | | | | | |
| 195 | Q | | | | | |
| 196 | A | G | | | | |
| 197 | A | | | | | |
| 198 | M | L | | | | |
| 199 | Q | E | H | | | |

and

TABLE 4

| AA no. | AA sequence | Naturally occurring AA's at each AA position | | | | | | |
|---|---|---|---|---|---|---|---|---|
| 233 | G | | | | | | | |
| 234 | S | A | | | | | | |
| 235 | D | | | | | | | |
| 236 | I | | | | | | | |
| 237 | A | | | | | | | |
| 238 | G | | | | | | | |
| 239 | T | A | S | | | | | |
| 240 | T | S | | | | | | |
| 241 | S | T | | | | | | |
| 242 | T | N | S | | | | | |
| 243 | L | P | V | Q | | | | |
| 244 | Q | A | H | | | | | |
| 245 | E | | | | | | | |
| 246 | Q | H | | | | | | |
| 247 | I | L | V | M | | | | |
| 248 | G | A | Q | T | N | R | H | I |
| 249 | W | | | | | | | |

TABLE 4-continued

| AA no. | AA sequence | Naturally occurring AA's at each AA position |
|---|---|---|
| 250 | M | T |
| 251 | T | S |

Several modified peptides have been synthesized in order to determine unique sequences which are both specific and sensitive towards HIV-1.

DESCRIPTION OF THE INVENTION

The peptides according to the invention are originating from the four different conserved areas of the HIV-1 gag protein p17 and p24 which are described above, having the properties of maintaining the uniqueness of the HIV-1-epitope. Further the new peptides according to the invention possess no recognized cytotoxic T lymphocyte (CTL) antagonistic effect and shall have at least one potential CTL epitope.

The peptides, according to the invention, which have met the above criteria are selected from the following groups;

(SEQ ID NO: 1)

$Xaa_1$ $Xaa_2$ $Xaa_3$ $Xaa_4$ $Xaa_5$ $Xaa_6$ $Xaa_7$ Gln Leu Gln $Xaa_{11}$ $Xaa_{12}$ $Xaa_{13}$ $Xaa_{14}$ $Xaa_{15}$ $Xaa_{16}$ $Xaa_{17}$ $Xaa_{18}$ $Xaa_{19}$ $Xaa_{20}$ $Xaa_{21}$ wherein the amino acids of the chain could have the following meanings;

Xaa in position 1 of the peptide derivate is His, Lys or Arg,

Xaa in position 2 is Ile, Leu, Val or Met,

Xaa in position 3 is Ile or Val,

Xaa in position 4 is Trp or Tyr,

Xaa in position 5 is Ala or Leu,

Xaa in position 6 is Ser, Thr, Arg or Asn,

Xaa in position 7 is Arg or Ser,

Xaa in position 11 is Arg, Lys, Gly or Asn,

Xaa in position 12 is Phe, Ser or Tyr

Xaa in position 13 is Ala, Thr or Ser

Xaa in position 14 is Val, Leu, Ile or Cys,

Xaa in position 15 is Asn, Asp or Ser,

Xaa in position 16 is Pro, Arg or Ser,

Xaa in position 17 is Gly, Ser, Ala, Asp or Asn

Xaa in position 18 is Leu or Phe,

Xaa in position 19 is Leu or Met,

Xaa in position 20 is Glu, Gly, Asp or Ile,

Xaa in position 21 is Thr, Ser or Ala the peptide comprises at least six consecutive amino acids of the sequence of SEQ ID NO: 1, (SEQ ID NO: 4)

$Xaa_1$ $Xaa_2$ $Xaa_3$ $Xaa_4$ $Xaa_5$ $Xaa_6$ $Xaa_7$ Gly $Xaa_9$ Leu

Val-Z-Tyr $Xaa_{13}$ $Xaa_{14}$ $Xaa_{15}$ $Xaa_{16}$ $Xaa_{17}$ $Xaa_{18}$ $Xaa_{19}$ $Xaa_{20}$ $Xaa_{21}$ Ala $Xaa_{23}$ $Xaa_{24}$ $Xaa_{25}$ $Xaa_{26}$ wherein the amino acids of the chain have the following meaning;

Xaa in position 1 is Pro, Tyr or Phe

Xaa in position 2 is Ile, Val or Leu,

Xaa in position 3 is Ile, Ala, Val, Met or Leu

Xaa in position 4 is Gln, Ser, Thr or Val

Xaa in position 5 is Asn, Asp or Thr

Xaa in position 6 is Ile, Ala, Leu or Met

Xaa in position 7 is Gln, Glu Lys or Gly

Xaa in position 9 is Gln or Ile

Xaa in position 13 is omitted

Xaa in position 14 is Ala, Ser, Asn, Val or Pro

Xaa in position 15 is Ile, Leu, Met or Val,

Xaa in position 16 is Ser or Thr

Xaa in position 17 is Pro or Ala,

Xaa in position 18 is Arg or Lys,

Xaa in position 19 is Thr or Ser

Xaa in position 20 is Leu or Ser

Xaa in position 21 is Asn, Phe or Val,

Xaa in position 23 is Trp, Tyr, Gly or none

Xaa in position 24 is Val, Leu, Gly or none

Xaa in position 25 is Lys, Arg, Gly or none

Xaa in position 26 is Val, Ala, Cys, Gly or none wherein the sequence of SEQ ID NO: 4 comprises at least six consecutive amino acids and —Z— is optional and have the meaning PEG, modified PEG and/or $[Gly]_n$, wherein n=1, 2 or 3, (SEQ ID NO: 9)

$Xaa_1$ Ala $Xaa_3$ $Xaa_4$ $Xaa_5$ Ala $Xaa_7$ $Xaa_8$ $Xaa_9$ Leu Leu $Xaa_{12}$ $Xaa_{13}$ $Xaa_{14}$-Z-$Xaa_{15}$ $Xaa_{16}$ His Gln $Xaa_{19}$ Ala $Xaa_{21}$ $Xaa_{22}$ wherein Xaa in position 1 is Tyr, Trp, Phe or Gly Xaa in position 3 is Thr, Ala, Val, Ile or Leu Xaa in position 4 is Pro or Ser Xaa in position 5 is Gln, His, Gly, Thr, Ser or Tyr Xaa in position 7 is Leu, Ile or Val Xaa in position 8 is Asn or Tyr Xaa in position 9 is Thr, Met, Leu or Ala Xaa in position 12 is Ser, Thr or Asn Xaa in position 13 is Thr, Ile, Val or Ala Xaa in position 14 is Val or Ile Xaa in position 15 is Gly or none Xaa in position 16 is Gly or none Xaa in position 19 is Ala or Gly Xaa in position 21 is Met, Leu, Cys or none Xaa in position 22 is Gln, Glu, His, Gly or none wherein the sequence of SEQ ID NO: 9 consists of at least six consecutive amino acids and the linker —Z— is optional and have the meaning PEG, modified PEG and/or $[Gly]_n$, wherein n=1, 2 or 3, (SEQ ID NO: 15)

$Xaa_1$ $Xaa_2$ Ala Leu Ala Gly $Xaa_7$ $Xaa_8$ $Xaa_9$ Leu $Xaa_{11}$ $Xaa_{12}$ $Xaa_{13}$ $Xaa_{14}$ $Xaa_{15}$ $Xaa_{16}$ $Xaa_{17}$ $Xaa_{18}$ $Xaa_{19}$ $Xaa_{20}$ $Xaa_{21}$ wherein the Xaa in position 1 is Trp or Tyr Xaa in position 2 is Ser or Ala Xaa in position 7 is Thr, Ala or Ser Xaa in position 8 is Ser or Thr Xaa in position 9 is Ser or Thr Xaa in position 11 is Leu, Pro, Val or Gln Xaa in position 12 is Gln, Ala or His Xaa in position 13 is Glu or Gly Xaa in position 14 is Gln or His Xaa in position 15 is Ile, Leu, Val or Met Xaa in position 16 is Gly, Ala, Gin, Thr, Asn, Arg, His or Ile Xaa in position 17 is Trp or Tyr Xaa in position 18 is Thr, Met, Leu or Ile Xaa in position 19 is Thr or Ser Xaa in position 20 is Cys, Gly or none Xaa in position 21 is Gly or none wherein the sequence of SEQ ID NO: 15 consists of at least six consecutive amino acids, the terminal ends of the sequences may be free carboxyl- or amino groups, amides, acyls, acetyls or salts thereof, two or more of the Cys residues may form part of an interchain disulphide binding, a —S—$(CH_2)_p$—S— or a —$(CH_2)_p$-bridge wherein p=1-8, optionally intervened by one or more hetero atoms such as O, N or S and/or the said peptide sequences are immobilized to a solid support.

The new peptide sequences have the potential to serve as a good antigen wherein the antigen comprises at least one peptide selected from the group of sequences of SEQ ID NO: 1, SEQ ID NO: 4, SEQ ID NO: 9 or SEQ ID NO: 15. The antigenicity may be adapted through adjusting the ratio or concentration of different peptides or size of the peptides by for instance dimerization or polymerization and/or immobilization to a solid phase. The antigen comprises two or more polypeptide sequences, according to the invention, which are either linked by a bridge for instance a disulphide bridge between the Cys residues of the chains or bridges like $C_1$-$C_8$ alkylen possibly intervened by one or more heteroatoms like O, S, or N or preferably they are unlinked. The chains may be immobilized to a solid phase in monomeric, dimeric or oligomeric forms. Further amino acids may be added to the ends in order to achieve an <<arm>> to facilitate immobilization.

PEG is polyethylene glycol $(HO(CH_2CH_2O)_mH$ and can be part of the linker —Z—, optionally PEG is modified by a dicarboxylic acid $(HO(CH_2CH_2O)_mCO(CH_2)_oCOOH)$ or a terminal carboxylic group $(HO(CH_2CH_2O)_{m-1}CH_2COOH)$ where m=1-10 and o=2-6, prior to linking.

The linker —Z— can either consist of PEG, modified PEG, or a combination thereof and/or one or more Gly residues combined. Alternatively the linker —Z— can consist of a Gly-bridge $[Gly]_n$ where n=1, 2 or 3.

All amino acids in the peptides of the invention can be in both D- or L-form, although the naturally occurring L-form is preferred.

The C- and N-terminal ends of the peptide sequences could deviate from the natural sequences by modification of the terminal $NH_2$-group and/or COOH-group, they may for instance be acylated, acetylated, amidated or modified to provide a binding site for a carrier or another molecule.

The peptides according to the invention are consisting of at least 6 amino acids, preferably between 10 and 30 amino acids. They are covering all natural variation of amino acids in the identified positions.

The polypeptide antigen according to the invention is either in a free or in a carrier-bound form. The carrier or solid phase to which the peptide is optionally bound can be selected from a vide variety of known carriers. It should be selected with regard to the intended use of the immobilized polypeptide as a diagnostic antigen or as an immunizing component in a vaccine.

Examples of carriers that can be used for e.g. diagnostic purposes are magnetic beads or latex of co-polymers such as styrene-divinyl benzene, hydroxylated styrene-divinyl benzene, polystyrene, carboxylated polystyrene, beads of carbon black, non-activated or polystyrene or polyvinyl chloride activated glass, epoxy-activated porous magnetic glass, gelatine or polysaccharide particles or other protein particles, red blood cells, mono or polyclonal antibodies or fab fragments of such antibodies.

According to a further embodiment of the present invention, the antigens may form part of a vaccine possibly combined with carriers, adjuvants or combined with other immunostimulating elements such as canarypox virus carrying the env gene. Examples of carriers and/or adjuvants for vaccine purposes are other proteins such as human or bovine serum albumin and keyhole limpet haemocyanin and fatty acids. Immunostimulatory materials may be divided into three groups; adjuvants, carriers for antigens and vehicles. Examples of adjuvants include aluminum hydroxyd, aluminum salts, saponin, muramyl di and tripeptides, monophosphoryl lipid A, palmitic acid, *B. pertussis* and various cytokines including the Th1 cytokine IL-12 and IL-1. A number of protein toxins can be used to carry passenger proteins across cellular membranes into the cytosol, which are useful in developing CTL vaccines. Carriers include bacterial toxoids such as inactivated tetanus and cholera toxins, genetically detoxified bacterial toxins such as heat labile enterotoxin from *E. coli*, fatty acids, live vectors such as polio chimeras and hybrid proteins that form particulates for example yeast retrotransposon hybrid TY particles and HBcAg particles. Vehicles which are frequently occurring components in modern vaccines are consisting of mineral oil emulsion, Freunds complete and incomplete adjuvant, vegetable oil emulsions, nonionic block co-polymer surfactants, squalene or squalane, lipopeptides, liposomes and biodegradable microspheres. Two recent adjuvants which possess significant potential for the development of new vaccines include an oil-in-water microemulsion (MF59) and polymeric microparticles. Any substance that can enhance the immunogenicity of the antigen may be used and several further alternatives of carriers or adjuvants are given in the US or European Pharmacopoeia.

A suitable formulation of the antigen for immunostimulatory uses may also comprise interferons such as INF-γ, antiviral chemokines or haematopoietic growth factors such as granulocyte macrophage growth (colony stimulating) factor.

Another approach in order to enhance the stimulation and absorption in for instance the intestine is to administer the peptides of the invention, with small peptides such as di, tri or tetrapeptides. These peptides can be administered in addition to or in combination with the peptides of the invention. Preferably the peptides are administered together with the tripeptide YGG, consisting of amino acids in the D- or L-forms, preferably in the D-form.

Recent approaches to non-parenteral delivery of vaccines, for instance via mucosa include; gene fusion technology to create non-toxic derivatives of mucosal adjuvants, genetically inactivated antigens with a deletion in an essential gene, co-expression of an antigen and a specific cytokine that is important in the modulation and control of a mucosal immune response, and genetic material itself that would allow DNA or RNA uptake and its endogenous expression in the host cells.

One approach for developing durable responses where cell-mediated immunity is required, is to vaccinate with plasmid DNA encoding one or more specific antigen(s).

In order to protect against HIV infection, vaccines should induce both mucosal and systemic immune responses and could be administered by any convenient route, parenterally or non-parenterally, such as subcutanously, intracutanously, intravenously, intramuscularly, perorally, mucosally or intranasally for example.

In a preferred embodiment of the vaccine according to the present invention it comprises antigens containing at least one of the peptides selected from the groups of SEQ ID NO: 1, 4, 9 and 15, more preferred different peptides occur in equal amounts.

In a further preferred embodiment the vaccine composition contains the antigens;

```
RLIYATRQLQRFAVNPGLLIT-NH2        (SEQ ID NO: 3)

FILQNIEGQLVGGGYAISPRTLVAGGGG     (SEQ ID NO: 6)

YAIPQALNTLLNTVGGHQAA-NH2         (SEQ ID NO: 11)
and

WSALAGTTSLLQGQLGWIT-NH2          (SEQ ID NO: 14)
```

The sequences contribute with CTL-epitopes and can activate the cellular immune system. The amino acid changes implemented within the frame of the CTL-epitopes are designed to achieve enhanced binding. Other amino acid changes have been conducted in order to facilitate the synthesis of the peptide and/or to increase the solubility of the peptide.

A method for detecting antibodies, induced by HIV-1 or HIV-1 specific peptides or proteins, in a sample of body fluid using the present antigens is a further embodiment of the invention. Also immunoassay kit designed for this detection and antibodies capable of selectively reacting with the said antigens are encompassed by the present invention.

Description of the Preparation of the Peptides

The peptides of the invention can be produced by any known method of producing a linear amino acid sequence, such as recombinant DNA techniques. A nucleic acid sequence which encodes a peptide of the invention or a multimer of the said peptides, is introduced into an expression vector. Suitable expression vectors are for instance plasmids, cosmids, viruses and YAC (yeast artificial chromosome) which comprise necessary control regions for replication and expression. The expression vector may be stimulated to expression in a host cell. Suitable host cells are for example bacteria, yeast cells and mammalian cells. Such techniques are well known in the art and described for instance by Sambrook et al., Molecular Cloning: A Laboratory Manual, Cold Spring Harbor Laboratory Press, Cold Spring Harbor, 1989. Other well-known techniques are degradation or synthesis by coupling of one amino acid residue to the next one in liquid phase or preferably on a solid phase (resin) for instance by the so-called Merrifield synthesis. See for instance Barany and Merrifield in the Peptides, Analysis, Synthesis, Biology, Vol. 2, E. Gross and Meinhofer, Ed. (Acad. Press, N.Y., 1980), Kneib-Coronier and Mullen Int. J. Peptide Protein Res., 30, p. 705-739 (1987) and Fields and Noble Int. J. Peptide Protein Res., 35, p. 161-214 (1990).

In case a linked or cyclic peptide is desired, the amino acid sequence is subjected to a chemical oxidation step in order to cyclize or link the two cysteine residues between two peptide sequences, when the appropriate linear amino acid sequences are synthesized, see Akaji et al., Tetrahedron Letter, 33, 8, p. 1073-1076, 1992.

General Description of Synthesis

All peptide derivatives prepared in the Examples given below were synthesized on a Milligen 9050 Peptide Synthesizer using a standard program. The resin used was Tenta Gel P RAM with a theoretical loading 0.20 meq/g (RAPP POLYMERE GmbH, Tübingen). The final product of the synthesis was dried in vacuo overnight. The peptide was then cleaved from the resin by treatment with 90% trifluoroacetic acid in the presence of ethane dithiol (5%) and water (5%) as scavengers (1.5 hours at RT). Then the resin was filtered and washed on filter with additional trifluoroacetic acid (100%) (2×20 ml). The combined filtrates were evaporated in vacuo (water bath at RT) and the residue was triturated with ethyl ether (200 ml) and the precipitated product filtered off. The solid was promptly dissolved on filter with glacial acetic acid (100 ml) and added to 1.5 l of 20% acetic acid in methanol and treated with 0.1 M solution of iodine in methanol until a faint brown colour remained. Then Dowex 1×8 ion exchange in acetate form (15 g) (Bio-Rad, Richmond, Calif.) was added and the mixture filtered. The filtrate was evaporated and the residue freeze-dried from acetic acid. The product was then purified by reversed phase liquid chromatography on a column filled with Kromasil® 100-5 C8 (EKA Nobel, Surte, Sweden) in a suitable system containing acetonitrile in 0.1% trifluoroacetic acid water solution. The samples collected from the column were analyzed by analytical high performance liquid chromatography (HPLC) (Beckman System Gold, USA) equipped with a Kromasil® 100-5 C8 Column (EKA Nobel, Surte, Sweden). Fractions containing pure substance were pooled, the solvent was evaporated and the product freeze-dried from acetic acid. The final HPLC analysis was performed on final product, and the structure of the peptide was confirmed by amino acid analysis and mass spectrometry (LDI-MS).

All amino acids used during the synthesis were L-amino acids and they were protected with a fluorenylmethoxy-carbonyl group at the α-amino function. The side chains were protected as follows:

Cys(Trt), Gln(Trt), Glu(OtBu), Thr(tBu).

The abbreviations, within the brackets are:

Trt=triphenylmethyl t-Bu=tert. Butyl

OtBu=tert. Butylester

The amino acid derivatives was supplied by Bachem A G, Switzerland.

EXAMPLE 1

Preparation of H L I Y L T R Q L Q R F A L N P G L L I T—$NH_2$ (SEQ ID NO: 2).

The peptide is synthesized in amide form, from corresponding starting materials according to the general description of synthesis. The purity is determined by HPLC analysis and the structure is confirmed by amino acid analysis and mass spectrometry (LDI-MS).

EXAMPLE 2

Preparation of R L I Y A T R Q L Q R F A V N P G L L I T—$NH_2$ (SEQ ID NO: 3).

The peptide was synthesized in amide form, from corresponding starting materials according to the general description of synthesis. The purity was determined by HPLC analysis and the structure was confirmed by amino acid analysis and mass spectrometry (LDI-MS).

Purity (HPLC): more than 97% (single impurities less than 1%)

Molecular weight (free base): 2442.9

EXAMPLE 3

Preparation of Y I L Q N I E G Q L V G G G Y A I S P R T L V A Y L R G—$NH_2$ (SEQ ID NO: 5). The peptide is synthesized in amide form, from the corresponding starting materials according to the general description of synthesis. The purity is determined by HPLC analysis and the structure is confirmed by amino acid analysis and mass spectrometry (LDI-MS).

EXAMPLE 4

Preparation of F I L N I E G Q L G G G G Y A I S P R T L V A G G G G (SEQ ID NO: 6). The peptide was synthesized from the corresponding starting materials according to the general description of synthesis. The purity was determined by HPLC analysis and the structure was confirmed by amino acid analysis and mass spectrometry (LDI-MS).

Purity (HPLC): more than 94%

Molecular weight (free base): 2745

Molecular formula: $C_{123}H_{198}O_{37}N_{34}$

EXAMPLE 5

Reference Example

Preparation of a nativ p24 sequence P I V Q N I E G Q M V H Q A I S P R T L N A W V K V (SEQ ID NO: 7). The peptide was synthesized from the corresponding starting materials according to the general description of synthesis. The purity was determined by HPLC analysis and the structure was confirmed by amino acid analysis and mass spectrometry (LDI-MS).

Purity (HPLC): approx. 85%

Molecular weight (free base): 2929

Molecular formula: $C_{131}H_{214}O_{36}N_{38}S$

EXAMPLE 6

Preparation of F I L Q N I Q G Q L V G G G Y A I S P R T L V A G—$NH_2$ (SEQ ID NO: 8).

The peptide was synthesized in amide form, from corresponding starting materials according to the general description of synthesis. The purity was determined by HPLC analysis and the structure was confirmed by amino acid analysis and mass spectrometry (LDI-MS).

Purity (HPLC): more than 97% (single impurity less than 1%)

Molecular weight (free base): 2572.0

EXAMPLE 7

Reference Example

Preparation of a nativ p24 sequence G A T P Q D L N T M L N T V G G H Q A A—$NH_2$ (SEQ ID NO: 10). The peptide was synthesized in amide form, from the corresponding starting materials according to the general description of synthesis. The purity was determined by HPLC analysis and the structure was confirmed by amino acid analysis and mass spectrometry (LDI-MS).

Purity (HPLC): 98%

Molecular weight (free base): 1995.2

Molecular formula: $C_{82}H_{135}O_{29}N_{27}S$

EXAMPLE 8

Preparation of Y A I P Q A L N T L L N T V G G H Q A A—$NH_2$ (SEQ ID NO: 11).

The peptide was synthesized in amide form, from the corresponding starting materials according to the general description of synthesis. The purity was determined by HPLC analysis and the structure was confirmed by amino acid analysis and mass spectrometry (LDI-MS).

Purity (HPLC): 98%

Molecular weight (free base): 2051.4

Molecular formula: $C_{91}H_{147}O_{27}N_{27}$

EXAMPLE 9

Preparation of F A I P Q A L N T L L N T V G G G G H Q A A C G—$NH_2$ (SEQ ID NO: 12). The peptide is synthesized in amide form, from the corresponding starting materials according to the general description of synthesis. The purity is determined by HPLC analysis and the structures is confirmed by amino acid analysis and mass spectrometry (LDI-MS).

EXAMPLE 10

Reference Example

Preparation of a nativ p24 sequence G S D I A G T T S T L Q E Q I G W M T—$NH_2$ (SEQ ID NO: 13). The peptide was synthesized in amide form, from the corresponding starting materials according to the general description of synthesis.

The purity was determined by HPLC analysis and the structure was confirmed by amino acid analysis and mass spectrometry (LDI-MS).

Purity (HPLC): 90%

Molecular weight (free base): 1995.2

Molecular formula: $C_{84}H_{135}O_{31}N_{23}S$

EXAMPLE 11

Preparation of W S A L A G T T S L L Q G Q L G W I T—$NH_2$ (SEQ ID NO: 14).

The peptide was synthesized in amide form, from the corresponding starting materials according to the general description of synthesis. The purity was determined by HPLC analysis and the structure was confirmed by amino acid analysis and mass spectrometry (LDI-MS).

Purity (HPLC): more than 97% (single impurities less than 1%)

Molecular weight (free base): 2007.3

EXAMPLE 12

Reference Example

Preparation of a nativ p17 sequence H I V W A S R E L E R F A V N P G L L E V T—$NH_2$ (SEQ ID NO: 16). The peptide was synthesized in amide form, from corresponding starting materials according to the general description of synthesis. The purity was determined by HPLC analysis and the structure was confirmed by amino acid analysis and mass spectrometry (LDI-MS).

Purity (HPLC): more than 95%

Molecular weight (free base): 2436.8

EXAMPLE 13

Reference Example

Preparation of a nativ p24 sequence P I V Q N I Q G Q M V H Q A I S P R T L N A W—$NH_2$ (SEQ ID NO: 17). The peptide was synthesized in amide form, from corresponding starting materials according to the general description of synthesis. The purity was determined by HPLC analysis and the structure was confirmed by amino acid analysis and mass spectrometry (LDI-MS).

Purity (HPLC): approximately 93%

Molecular weight (free base) 2601.0

EXAMPLE14

Dimerisation via Disulphide Bridge

The peptide sequences are linked via an oxidation step to form a dipeptide wherein the cysteine residues form a disulphide bridge. The bridge can for instance be formed by oxidation with $I_2$ as follows;

Equal amounts of the peptides are dissolved in acetic acid/methanol (1:4) and 0.1 M $I_2$ in methanol is added yielding a mixture of the dimer.

EXAMPLE 15

A vaccine comprising the peptides of the SEQ ID NO: 3, 6, 11 and 14 is prepared. The freeze-dried peptides are dissolved in sterile water at a final concentration of 4 mg/ml. The final salt concentration of the solution is physiological compatible. A preparation of a granulocyte-macrophage-colony stimulating factor (GM-CSF) is also prepared, according to the manufacturers directions for use, to a final concentration of 0.3 mg/ml. The two solutions are administered intracutaneously. A typical injection dose is 100 μl.

EXAMPLE 16

An antigen solution or suspension is mixed with equal parts of Freund's adjuvant of Behring, complete or incomplete, and is then finely emulsified by being drawn up into, and vigorously pressed out of, an injection syringe, or with a homogenator. The emulsion should remain stable for at least 30 minutes. The antigen-adjuvant emulsions is best injected subcutaneously as a depot.

EXAMPLE 17

Immunoassay for Detection of Antibodies Induced by HIV-1

The magnetic particle reagents are to be prepared according to the manufacturers recommended protocol. Dynal AS, is the manufacturer of the Dynabeads, which are employed. The magnetic particles coated with ligand are called Reagent 1. A peptide according to the invention is covalently coupled to the pre-activated surface of the magnetic particles. It is also possible to physically absorb the peptide to the surface of the magnetic particles. The concentration of particles in Reagent 1 is within the range from 1 mg/ml to 15 mg/ml. The particle size varies between 0.2 μm to 15 μm. The concentration of peptides is within the range from 0.01 mg/mg particle to 1 mg/mg particle.

The anti human Ig Alkaline Phosphatase (AP) conjugated antibody reagent is prepared according to the recommended protocol of Dako AS. This protocol is a standard procedure in this field. This reagent is called Reagent 2.

The substrate solution phenolphtalein-monophosphate is to be prepared according to the recommended protocol of Fluka AG. This protocol is a standard procedure in this field. The substrate solution is called Reagent 3.

The washing and incubation buffer which is used is standard 0.05 M tris-base buffer with the following additional compounds; Tween 20 (0.01% to 0.1%), glycerol (0.1% to 10%) and sodium chloride (0.2% to 0.1%).

The assay procedure comprises an incubation step wherein 1 drop of Reagent 1 is mixed with 2 drops of washing buffer in each well. After mixing, 30 μl of sample is added and the solution is incubated for 5 minutes. The magnetic particles can be trapped by a magnet and the liquid removed, before the magnet is separated. Then the wells are washed twice in 4 drops of washing solution, before incubation with Reagent 2. 1 drop of Reagent 2 is added with 2 drops of washing buffer and the solution is incubated for 5 minutes. The magnetic particles can be trapped by a magnet and the liquid removed, before the magnet is separated. Then the washing step is repeated before incubation with Reagent 3. 2 drops of Reagent 3 is added to each well and the solution is incubated for 3 minutes. The results can be read against a white background. Positive results are red (3+=strong red) whereas negative results are clearly light yellow/brown solutions as obtained in the negative control.

The immunoassay kit could be used in detection of antibodies, induced either by HIV virus or HIV-specific peptides or proteins, for instance the peptides of the present invention.

EXAMPLE 18

Therapeutic or Prophylactic Vaccine

At least one of the polypeptides of the invention, selected from the group of sequences, SEQ ID NO: 1, SEQ ID NO: 4, SEQ ID NO: 9 and SEQ ID NO: 15 can be used to form antigens and be the active principle of a prophylactic or therapeutic vaccine intended to provide protection against the human immunodeficiency virus type 1 (HIV-1). The vaccine may include compounds having beneficial effects in protecting or stimulating the hosts immune system (human being or vertebrate animal) for instance interleukins, interferons, granulocyte macrophage growth factors, haematopoietic growth factors or similar. Preferably the vaccine composition further contain an adjuvant or vehicle, more preferably the adjuvant or vehicle is Monophosphoryl Lipid A (MPL®) possibly with alum, Freund's adjuvant (complete or incomplete) or aluminum hydroxyd. The optimal amount of adjuvant/vehicle will depend on the type(s) which is/are chosen.

The peptides of the invention might be modified by C-terminal addition of a single fatty acid such as a single palmitoyl chain to form a lipopeptide vaccine. Further the lipopeptides can be introduced into liposome membranes by the freeze-thaw method resulting in liposomes bearing the peptide ligands on their surface.

The peptide or vaccine formulation can be freeze-dried prior to storage. The freeze-dried peptides can be dissolved in sterile water to a final concentration of from 0.1 to 100 mg/ml. The vaccine may be stored preferably at low temperature, in ampoules containing one or more dosage units, ready for use. A typical dosage unit of the peptide according to the invention is within the concentration range: 0.05 μg-1 mg per kg bodyweight, preferably within 0.15 μg-0.15 mg per kg body weight. Persons skilled in the art will appreciate that a suitable dose will depend on the body weight of the pasient, the type of disease, severity of condition, administration route and several other factors. When used as a therapeutic vaccine the vaccine will typically initially be administered about 12 times, through injections. Further boosters might follow and in extreme cases be administered throughout the patients life. In preparation of an injection solution the peptides are dissolved in sterile water to a final concentration of 1 mg/ml per peptide. Typically an injection volume is 100 μl to 200 μl (2×100 μl). The peptide is preferably co-administered with a suitable adjuvant and/or a granulocyte-macrophage growth factor, for instance Leucomax® <<Shering Plough>> made within a concentration range of from 0.1 to 1 mg/ml, or according to the manufacturers recommendations. Particulary preferred is a combination therapy where the present peptides are administered together with the peptides described in the published International patent application no. PCT/NO00/00075 filed Mar. 2, 2000 and/or the co pending Norwegian Patent Application No. 2000 4412. The peptides may be administered sequentially or simultaneously. Suitable administration may be intracutane, subcutane, intravenous, peroral, intramuscular, intranasal, mucosal or any other suitable route. Booster administrations may be required in order to maintain protection. For persons skilled in the art it will be understood that the vaccine compositions according to the invention are useful not only in prevention of infection, but also in treatment of infection.

No toxic effects of the peptides according to the invention, are observed when injected in mice in a dosage of 100 μg per kg body weight.

The above Examples are only meant as illustrating the invention. It must be understood that a person skilled in the art can modify the peptides, antigens and vaccines herein described without deviating from the concept and scope of this invention as set forth in the claims.

The invention claimed is:

1. An isolated peptide from HIV-1 Gag p24 protein, which comprises at least one amino acid sequence which contains modifications compared with the native sequence and is selected from the group consisting of:

$Xaa_1$ $Xaa_2$ $Xaa_3$ $Xaa_4$ $Xaa_5$ $Xaa_6$ $Xaa_7$ Gly $Xaa_9$ Leu Val $Xaa_{12}$ $Xaa_{13}$ $Xaa_{14}$ Tyr $Xaa_{16}$ $Xaa_{17}$ $Xaa_{18}$ $Xaa_{19}$ $Xaa_{20}$ $Xaa_{21}$ $Xaa_{22}$ $Xaa_{23}$ Ala $Xaa_{25}$ $Xaa_{26}$ $Xaa_{27}$ $Xaa_{28}$ (SEQ ID NO: 4), wherein $Xaa_1$ is Pro, Tyr or Phe, $Xaa_2$ is Ile, Val or Leu, $Xaa_3$ is Ile, Leu, Val, Ala or Met, $Xaa_4$ is Gln, Ser, Thr or Val, $Xaa_5$ is Asn, Asp or Thr, $Xaa_6$ is Ile, Ala, Leu or Met, $Xaa_7$ is Gln, Glu, Lys or Gly, $Xaa_9$ is Gln or Ile, $Xaa_{12}$ is none, $Xaa_{13}$ is none, $Xaa_{14}$ is none, $Xaa_{16}$ is Ala, Ser, Asn, Val or Pro, $Xaa_{17}$ is Ile, Leu, Met or Val, $Xaa_{18}$ is Ser or Thr, $Xaa_{19}$ is Pro or Ala, $Xaa_{20}$ is Arg or Lys,
$Xaa_{21}$ is Thr or Ser,
$Xaa_{22}$ is Leu or Ser,
$Xaa_{23}$ is Asn, Phe or Val,
$Xaa_{25}$ is Trp, Tyr, Gly or none,
$Xaa_{26}$ is Val, Leu, Gly or none,
$Xaa_{27}$ is Lys, Arg, Gly or none,
$Xaa_{28}$ is Val, Ala, Cys, Gly or none;
$Xaa_1$ Ala $Xaa_3$ $Xaa_4$ $Xaa_5$ Ala $Xaa_7$ $Xaa_8$ $Xaa_9$ Leu Leu $Xaa_{12}$ $Xaa_{13}$ $Xaa_{14}$ $Xaa_{15}$ $Xaa_{16}$ $Xaa_{17}$ $Xaa_{18}$ $Xaa_{19}$ His Gln $Xaa_{22}$ Ala $Xaa_{24}$ $Xaa_{25}$ (SEQ ID NO: 9), wherein
$Xaa_1$ is Tyr, Trp, Phe or Gly,
$Xaa_3$ is Thr, Ala, Val, Ile or Leu,
$Xaa_4$ is Pro or Ser,
$Xaa_5$ is Gln, His, Gly, Thr, Ser or Tyr,
$Xaa_7$ is Leu, Ile or Val,
$Xaa_8$ is Asn or Tyr,
$Xaa_9$ is Thr, Met, Leu or Ala,
$Xaa_{12}$ is Ser, Thr or Asn,
$Xaa_{13}$ is Thr, Ile, Val or Ala,
$Xaa_{14}$ is Val or Ile,
$Xaa_{15}$ is none,
$Xaa_{16}$ is none,
$Xaa_{17}$ is none,
$Xaa_{18}$ is Gly or none,
$Xaa_{19}$ is Gly or none,
$Xaa_{22}$ is Ala or Gly,
$Xaa_{24}$ is Met, Leu, Cys or none,
$Xaa_{25}$ is Gln, Glu, His, Gly or none;
$Xaa_1$ $Xaa_2$ Ala Leu Ala Gly $Xaa_7$ $Xaa_8$ $Xaa_9$ Leu $Xaa_{11}$ $Xaa_{12}$ $Xaa_{13}$ $Xaa_{14}$ $Xaa_{15}$ $Xaa_{16}$ $Xaa_{17}$ $Xaa_{18}$ $Xaa_{19}$ $Xaa_{20}$ $Xaa_{21}$ (SEQ ID NO: 15), wherein
$Xaa_1$ is Trp or Tyr,
$Xaa_2$ is Ser or Ala,
$Xaa_7$ is Thr, Ala or Ser,
$Xaa_8$ is Ser or Thr,
$Xaa_9$ is Ser or Thr,
$Xaa_{11}$ is Leu, Pro, Val or Gln,
$Xaa_{12}$ is Gin, Ala or His,
$Xaa_{13}$ is Glu or Gly,
$Xaa_{14}$ is Gin or His,
$Xaa_{15}$ is Ile, Leu, Val or Met,
$Xaa_{16}$ is Gly, Ala, Gln, Thr, Asn, Arg, His or Ile,
$Xaa_{17}$ is Trp or Tyr,
$Xaa_{18}$ is Thr, Met, Leu or Ile,
$Xaa_{19}$ is Thr or Ser,
$Xaa_{20}$ is Cys, Gly or none,
$Xaa_{21}$ is Gly or none
wherein the terminal ends of the sequences may be free carboxyl- or amino groups, amides, acyls, acetyls or salts thereof,
two or more of the Cys residues may form part of an interchain disulphide binding, a —S—$(CH2)_p$—S— or a —$(CH2)_p$—-bridge wherein p=1-8 optionally intervened by one or more hetero atoms such as O, N and S and/or the said peptide sequences are immobilized to a solid support.

2. The isolated peptide according to claim 1, wherein the amino acid sequence of SEQ ID NO 4 is selected from the group consisting of SEQ ID NO: 5, SEQ ID NO: 6 and SEQ ID NO: 8.

3. The isolated peptide according to claim 1, wherein the amino acid sequence of SEQ ID NO: 9 is SEQ ID NO: 11.

4. The isolated peptide according to claim 1, wherein the amino acid sequence of SEQ ID NO: 15 is SEQ ID NO: 14.

5. An antigen comprising at least one peptide according to claim 1.

6. The antigen according to claim 5, which comprises at least one peptide selected from the group consisting of SEQ ID NO: 4, SEQ ID NO: 9 and SEQ ID NO: 15.

7. An immunogenic composition, comprising the antigen according to claim 5 with a pharmaceutically acceptable diluent and optionally an adjuvant, carrier and/or vehicle and optionally additional immunostimulatory compound(s).

8. The immunogenic composition according to claim 7, which comprises at least one peptide selected from the group consisting of SEQ ID NO: 4, SEQ ID NO: 9 and SEQ ID NO: 15.

9. The immunogenic composition according to claim 7, which comprises the peptides of SEQ ID NO: 11.

10. The immunogenic composition according to claim 7, wherein the peptides are dissolved in a sterile water solution and the optional immunostimulatory compound is a granulocyte macrophage colony stimulating factor.

11. The immunogenic composition according to claim 7, wherein the composition comprises an adjuvant selected from the group consisting of Monophosphoryl Lipid A (MPL), Freund's complete adjuvant or Freund's incomplete adjuvant and aluminum hydroxide.

12. An immunogenic composition, comprising the antigen according to claim 5, wherein the antigen is formulated as a lipopeptide and/or a liposome formulation.

13. A method of detecting antibodies, induced by a HIV or HIV-specific peptide(s) or protein(s), in a sample of body fluid, comprising subjecting the sample to an immunoassay, wherein the antigen(s) is/are selected from the peptides of claim 1.

14. An immunoassay kit for the detection of antibodies, induced by a HIV or HIV-specific peptides or proteins, in a sample of body fluid, comprising a diagnostic antigen which is the peptide of claim 1.

15. The immunogenic composition according to claim 8, which comprises at least one peptide of SEQ ID NO: 11.

* * * * *

SEQUENCE LISTING

```
<160> NUMBER OF SEQ ID NOS: 17

<210> SEQ ID NO 1
<211> LENGTH: 21
<212> TYPE: PRT
<213> ORGANISM: Artificial Sequence
<220> FEATURE:
<223> OTHER INFORMATION: Description of Artificial Sequence: HIV PEPTIDE
<220> FEATURE:
<221> NAME/KEY: Variant
<222> LOCATION: 1
<223> OTHER INFORMATION: His Lys or Arg
<220> FEATURE:
<221> NAME/KEY: Variant
<222> LOCATION: 2
<223> OTHER INFORMATION: Ile, Leu, Val or Met
<220> FEATURE:
<221> NAME/KEY: Variant
<222> LOCATION: 3
<223> OTHER INFORMATION: Ile or Val
<220> FEATURE:
<221> NAME/KEY: Variant
<222> LOCATION: 4
<223> OTHER INFORMATION: Trp or Tyr
<220> FEATURE:
<221> NAME/KEY: Variant
<222> LOCATION: 5
<223> OTHER INFORMATION: Ala or Leu
<220> FEATURE:
```

-continued

<221> NAME/KEY: Variant
<222> LOCATION: 6
<223> OTHER INFORMATION: Ser Thr Arg or Asn
<220> FEATURE:
<221> NAME/KEY: Variant
<222> LOCATION: 7
<223> OTHER INFORMATION: Arg or Ser
<220> FEATURE:
<221> NAME/KEY: Variant
<222> LOCATION: 8
<223> OTHER INFORMATION: Gln
<220> FEATURE:
<221> NAME/KEY: Variant
<222> LOCATION: 9
<223> OTHER INFORMATION: Leu
<220> FEATURE:
<221> NAME/KEY: Variant
<222> LOCATION: 10
<223> OTHER INFORMATION: Gln
<220> FEATURE:
<221> NAME/KEY: Variant
<222> LOCATION: 11
<223> OTHER INFORMATION: Arg Lys Gly or Asn
<220> FEATURE:
<221> NAME/KEY: Variant
<222> LOCATION: 12
<223> OTHER INFORMATION: Phe Ser or Tyr
<220> FEATURE:
<221> NAME/KEY: Variant
<222> LOCATION: 13
<223> OTHER INFORMATION: Ala Thr or Ser
<220> FEATURE:
<221> NAME/KEY: Variant
<222> LOCATION: 14
<223> OTHER INFORMATION: Val Leu Ile or Cys
<220> FEATURE:
<221> NAME/KEY: Variant
<222> LOCATION: 15
<223> OTHER INFORMATION: Asn Ser or Asp
<220> FEATURE:
<221> NAME/KEY: Variant
<222> LOCATION: 16
<223> OTHER INFORMATION: Pro Arg or Ser
<220> FEATURE:
<221> NAME/KEY: Variant
<222> LOCATION: 17
<223> OTHER INFORMATION: Gly Ser Ala Asp or Asn
<220> FEATURE:
<221> NAME/KEY: Variant
<222> LOCATION: 18
<223> OTHER INFORMATION: Leu or Phe
<220> FEATURE:
<221> NAME/KEY: Variant
<222> LOCATION: 19
<223> OTHER INFORMATION: Leu or Met
<220> FEATURE:
<221> NAME/KEY: Variant
<222> LOCATION: 20
<223> OTHER INFORMATION: Glu Gly Asp or Ile
<220> FEATURE:
<221> NAME/KEY: Variant
<222> LOCATION: 21
<223> OTHER INFORMATION: Thr Ser or Ala

<400> SEQUENCE: 1

```
Xaa Xaa Xaa Xaa Xaa Xaa Xaa Gln Leu Gln Xaa Xaa Xaa Xaa Xaa Xaa
  1               5                  10                  15

Xaa Xaa Xaa Xaa Xaa
            20
```

<210> SEQ ID NO 2
<211> LENGTH: 21
<212> TYPE: PRT
<213> ORGANISM: Artificial Sequence
<220> FEATURE:
<223> OTHER INFORMATION: Description of Artificial Sequence: HIV PEPTIDE -continued
<220> FEATURE:
<221> NAME/KEY: Variant
<222> LOCATION: 1
<223> OTHER INFORMATION: His
<220> FEATURE:
<221> NAME/KEY: Variant
<222> LOCATION: 2
<223> OTHER INFORMATION: Leu
<220> FEATURE:
<221> NAME/KEY: Variant
<222> LOCATION: 3
<223> OTHER INFORMATION: Ile
<220> FEATURE:
<221> NAME/KEY: Variant
<222> LOCATION: 4
<223> OTHER INFORMATION: Tyr
<220> FEATURE:
<221> NAME/KEY: Variant
<222> LOCATION: 5
<223> OTHER INFORMATION: Leu
<220> FEATURE:
<221> NAME/KEY: Variant
<222> LOCATION: 6
<223> OTHER INFORMATION: Thr
<220> FEATURE:
<221> NAME/KEY: Variant
<222> LOCATION: 7
<223> OTHER INFORMATION: Arg
<220> FEATURE:
<221> NAME/KEY: Variant
<222> LOCATION: 8
<223> OTHER INFORMATION: Gln
<220> FEATURE:
<221> NAME/KEY: Variant
<222> LOCATION: 9
<223> OTHER INFORMATION: Leu
<220> FEATURE:
<221> NAME/KEY: Variant
<222> LOCATION: 10
<223> OTHER INFORMATION: Gln
<220> FEATURE:
<221> NAME/KEY: Variant
<222> LOCATION: 11
<223> OTHER INFORMATION: Arg
<220> FEATURE:
<221> NAME/KEY: Variant
<222> LOCATION: 12
<223> OTHER INFORMATION: Phe
<220> FEATURE:
<221> NAME/KEY: Variant
<222> LOCATION: 13
<223> OTHER INFORMATION: Ala
<220> FEATURE:
<221> NAME/KEY: Variant
<222> LOCATION: 14
<223> OTHER INFORMATION: Leu
<220> FEATURE:
<221> NAME/KEY: Variant
<222> LOCATION: 15
<223> OTHER INFORMATION: Asn
<220> FEATURE:
<221> NAME/KEY: Variant
<222> LOCATION: 16
<223> OTHER INFORMATION: Pro
<220> FEATURE:
<221> NAME/KEY: Variant
<222> LOCATION: 17
<223> OTHER INFORMATION: Gly
<220> FEATURE:
<221> NAME/KEY: Variant
<222> LOCATION: 18
<223> OTHER INFORMATION: Leu
<220> FEATURE:
<221> NAME/KEY: Variant
<222> LOCATION: 19
<223> OTHER INFORMATION: Leu
<220> FEATURE:
<221> NAME/KEY: Variant
<222> LOCATION: 20

-continued

<223> OTHER INFORMATION: Ile
<220> FEATURE:
<221> NAME/KEY: Variant
<222> LOCATION: 21
<223> OTHER INFORMATION: Thr

<400> SEQUENCE: 2

```
His Leu Ile Tyr Leu Thr Arg Gln Leu Gln Arg Phe Ala Leu Asn Pro
  1               5                  10                  15

Gly Leu Leu Ile Thr
             20
```

<210> SEQ ID NO 3
<211> LENGTH: 21
<212> TYPE: PRT
<213> ORGANISM: Artificial Sequence
<220> FEATURE:
<223> OTHER INFORMATION: Description of Artificial Sequence: HIV PEPTIDE
<220> FEATURE:
<221> NAME/KEY: Variant
<222> LOCATION: 1
<223> OTHER INFORMATION: Arg
<220> FEATURE:
<221> NAME/KEY: Variant
<222> LOCATION: 2
<223> OTHER INFORMATION: Leu
<220> FEATURE:
<221> NAME/KEY: Variant
<222> LOCATION: 3
<223> OTHER INFORMATION: Ile
<220> FEATURE:
<221> NAME/KEY: Variant
<222> LOCATION: 4
<223> OTHER INFORMATION: Tyr
<220> FEATURE:
<221> NAME/KEY: Variant
<222> LOCATION: 5
<223> OTHER INFORMATION: Ala
<220> FEATURE:
<221> NAME/KEY: Variant
<222> LOCATION: 6
<223> OTHER INFORMATION: Thr
<220> FEATURE:
<221> NAME/KEY: Variant
<222> LOCATION: 7
<223> OTHER INFORMATION: Arg
<220> FEATURE:
<221> NAME/KEY: Variant
<222> LOCATION: 8
<223> OTHER INFORMATION: Gln
<220> FEATURE:
<221> NAME/KEY: Variant
<222> LOCATION: 9
<223> OTHER INFORMATION: Leu
<220> FEATURE:
<221> NAME/KEY: Variant
<222> LOCATION: 10
<223> OTHER INFORMATION: Gln
<220> FEATURE:
<221> NAME/KEY: Variant
<222> LOCATION: 11
<223> OTHER INFORMATION: Arg
<220> FEATURE:
<221> NAME/KEY: Variant
<222> LOCATION: 12
<223> OTHER INFORMATION: Phe
<220> FEATURE:
<221> NAME/KEY: Variant
<222> LOCATION: 13
<223> OTHER INFORMATION: Ala
<220> FEATURE:
<221> NAME/KEY: Variant
<222> LOCATION: 14
<223> OTHER INFORMATION: Val
<220> FEATURE:
<221> NAME/KEY: Variant -continued

```
<222> LOCATION: 15
<223> OTHER INFORMATION: Asn
<220> FEATURE:
<221> NAME/KEY: Variant
<222> LOCATION: 16
<223> OTHER INFORMATION: Pro
<220> FEATURE:
<221> NAME/KEY: Variant
<222> LOCATION: 17
<223> OTHER INFORMATION: Gly
<220> FEATURE:
<221> NAME/KEY: Variant
<222> LOCATION: 18
<223> OTHER INFORMATION: Leu
<220> FEATURE:
<221> NAME/KEY: Variant
<222> LOCATION: 19
<223> OTHER INFORMATION: Leu
<220> FEATURE:
<221> NAME/KEY: Variant
<222> LOCATION: 20
<223> OTHER INFORMATION: Ile
<220> FEATURE:
<221> NAME/KEY: Variant
<222> LOCATION: 21
<223> OTHER INFORMATION: Thr

<400> SEQUENCE: 3

Arg Leu Ile Tyr Ala Thr Arg Gln Leu Gln Arg Phe Ala Val Asn Pro
  1               5                  10                  15

Gly Leu Leu Ile Thr
            20


<210> SEQ ID NO 4
<211> LENGTH: 28
<212> TYPE: PRT
<213> ORGANISM: Artificial Sequence
<220> FEATURE:
<223> OTHER INFORMATION: Description of Artificial Sequence: HIV PEPTIDE
<220> FEATURE:
<221> NAME/KEY: Variant
<222> LOCATION: 1
<223> OTHER INFORMATION: Pro Tyr or Phe
<220> FEATURE:
<221> NAME/KEY: Variant
<222> LOCATION: 2
<223> OTHER INFORMATION: Ile Val or Leu
<220> FEATURE:
<221> NAME/KEY: Variant
<222> LOCATION: 3
<223> OTHER INFORMATION: Ile Leu Val Ala or Met
<220> FEATURE:
<221> NAME/KEY: Variant
<222> LOCATION: 4
<223> OTHER INFORMATION: Gln Ser Thr or Val
<220> FEATURE:
<221> NAME/KEY: Variant
<222> LOCATION: 5
<223> OTHER INFORMATION: Asn Asp or Thr
<220> FEATURE:
<221> NAME/KEY: Variant
<222> LOCATION: 6
<223> OTHER INFORMATION: Ile Ala Leu or Met
<220> FEATURE:
<221> NAME/KEY: Variant
<222> LOCATION: 7
<223> OTHER INFORMATION: Gln Glu Lys or Gly
<220> FEATURE:
<221> NAME/KEY: Variant
<222> LOCATION: 8
<223> OTHER INFORMATION: Gly
<220> FEATURE:
<221> NAME/KEY: Variant
<222> LOCATION: 9
<223> OTHER INFORMATION: Gln or Ile
<220> FEATURE:
```

-continued

<221> NAME/KEY: Variant
<222> LOCATION: 10
<223> OTHER INFORMATION: Leu
<220> FEATURE:
<221> NAME/KEY: Variant
<222> LOCATION: 11
<223> OTHER INFORMATION: Val
<220> FEATURE:
<221> NAME/KEY: Variant
<222> LOCATION: 12
<223> OTHER INFORMATION: Gly or None or PEG Linker
<220> FEATURE:
<221> NAME/KEY: Variant
<222> LOCATION: 13
<223> OTHER INFORMATION: Gly or None or PEG Linker
<220> FEATURE:
<221> NAME/KEY: Variant
<222> LOCATION: 14
<223> OTHER INFORMATION: Gly or None or PEG Linker
<220> FEATURE:
<221> NAME/KEY: Variant
<222> LOCATION: 15
<223> OTHER INFORMATION: Tyr
<220> FEATURE:
<221> NAME/KEY: Variant
<222> LOCATION: 16
<223> OTHER INFORMATION: Ala Ser Asn Val or Pro
<220> FEATURE:
<221> NAME/KEY: Variant
<222> LOCATION: 17
<223> OTHER INFORMATION: Ile Leu Met or Val
<220> FEATURE:
<221> NAME/KEY: Variant
<222> LOCATION: 18
<223> OTHER INFORMATION: Ser or Thr
<220> FEATURE:
<221> NAME/KEY: Variant
<222> LOCATION: 19
<223> OTHER INFORMATION: Pro or Ala
<220> FEATURE:
<221> NAME/KEY: Variant
<222> LOCATION: 20
<223> OTHER INFORMATION: Arg or Lys
<220> FEATURE:
<221> NAME/KEY: Variant
<222> LOCATION: 21
<223> OTHER INFORMATION: Thr or Ser
<220> FEATURE:
<221> NAME/KEY: Variant
<222> LOCATION: 22
<223> OTHER INFORMATION: Leu or Ser
<220> FEATURE:
<221> NAME/KEY: Variant
<222> LOCATION: 23
<223> OTHER INFORMATION: Asn Phe or Val
<220> FEATURE:
<221> NAME/KEY: Variant
<222> LOCATION: 24
<223> OTHER INFORMATION: Ala
<220> FEATURE:
<221> NAME/KEY: Variant
<222> LOCATION: 25
<223> OTHER INFORMATION: Trp Tyr Gly or none
<220> FEATURE:
<221> NAME/KEY: Variant
<222> LOCATION: 26
<223> OTHER INFORMATION: Val Leu Gly or none
<220> FEATURE:
<221> NAME/KEY: Variant
<222> LOCATION: 27
<223> OTHER INFORMATION: Lys Arg Gly or none
<220> FEATURE:
<221> NAME/KEY: Variant
<222> LOCATION: 28
<223> OTHER INFORMATION: Val Ala Cys Gly or none

<400> SEQUENCE: 4

Xaa Xaa Xaa Xaa Xaa Xaa Xaa Gly Xaa Leu Val Xaa Xaa Xaa Tyr Xaa

-continued

```
 1               5                  10                  15

Xaa Xaa Xaa Xaa Xaa Xaa Xaa Ala Xaa Xaa Xaa Xaa
             20                  25
```

<210> SEQ ID NO 5
<211> LENGTH: 28
<212> TYPE: PRT
<213> ORGANISM: Artificial Sequence
<220> FEATURE:
<223> OTHER INFORMATION: Description of Artificial Sequence: HIV PEPTIDE
<220> FEATURE:
<221> NAME/KEY: Variant
<222> LOCATION: 1
<223> OTHER INFORMATION: Tyr
<220> FEATURE:
<221> NAME/KEY: Variant
<222> LOCATION: 2
<223> OTHER INFORMATION: Ile
<220> FEATURE:
<221> NAME/KEY: Variant
<222> LOCATION: 3
<223> OTHER INFORMATION: Leu
<220> FEATURE:
<221> NAME/KEY: Variant
<222> LOCATION: 4
<223> OTHER INFORMATION: Gln
<220> FEATURE:
<221> NAME/KEY: Variant
<222> LOCATION: 5
<223> OTHER INFORMATION: Asn
<220> FEATURE:
<221> NAME/KEY: Variant
<222> LOCATION: 6
<223> OTHER INFORMATION: Ile
<220> FEATURE:
<221> NAME/KEY: Variant
<222> LOCATION: 7
<223> OTHER INFORMATION: Glu
<220> FEATURE:
<221> NAME/KEY: Variant
<222> LOCATION: 8
<223> OTHER INFORMATION: Gly
<220> FEATURE:
<221> NAME/KEY: Variant
<222> LOCATION: 9
<223> OTHER INFORMATION: Gln
<220> FEATURE:
<221> NAME/KEY: Variant
<222> LOCATION: 10
<223> OTHER INFORMATION: Leu
<220> FEATURE:
<221> NAME/KEY: Variant
<222> LOCATION: 11
<223> OTHER INFORMATION: Val
<220> FEATURE:
<221> NAME/KEY: Variant
<222> LOCATION: 12
<223> OTHER INFORMATION: Gly
<220> FEATURE:
<221> NAME/KEY: Variant
<222> LOCATION: 13
<223> OTHER INFORMATION: Gly
<220> FEATURE:
<221> NAME/KEY: Variant
<222> LOCATION: 14
<223> OTHER INFORMATION: Gly
<220> FEATURE:
<221> NAME/KEY: Variant
<222> LOCATION: 15
<223> OTHER INFORMATION: Tyr
<220> FEATURE:
<221> NAME/KEY: Variant
<222> LOCATION: 16
<223> OTHER INFORMATION: Ala
<220> FEATURE:
<221> NAME/KEY: Variant
<222> LOCATION: 17

-continued

<223> OTHER INFORMATION: Ile
<220> FEATURE:
<221> NAME/KEY: Variant
<222> LOCATION: 18
<223> OTHER INFORMATION: Ser
<220> FEATURE:
<221> NAME/KEY: Variant
<222> LOCATION: 19
<223> OTHER INFORMATION: Pro
<220> FEATURE:
<221> NAME/KEY: Variant
<222> LOCATION: 20
<223> OTHER INFORMATION: Arg
<220> FEATURE:
<221> NAME/KEY: Variant
<222> LOCATION: 21
<223> OTHER INFORMATION: Thr
<220> FEATURE:
<221> NAME/KEY: Variant
<222> LOCATION: 22
<223> OTHER INFORMATION: Leu
<220> FEATURE:
<221> NAME/KEY: Variant
<222> LOCATION: 23
<223> OTHER INFORMATION: Val
<220> FEATURE:
<221> NAME/KEY: Variant
<222> LOCATION: 24
<223> OTHER INFORMATION: Ala
<220> FEATURE:
<221> NAME/KEY: Variant
<222> LOCATION: 25
<223> OTHER INFORMATION: Tyr
<220> FEATURE:
<221> NAME/KEY: Variant
<222> LOCATION: 26
<223> OTHER INFORMATION: Leu
<220> FEATURE:
<221> NAME/KEY: Variant
<222> LOCATION: 27
<223> OTHER INFORMATION: Arg
<220> FEATURE:
<221> NAME/KEY: Variant
<222> LOCATION: 28
<223> OTHER INFORMATION: Gly

<400> SEQUENCE: 5

```
Tyr Ile Leu Gln Asn Ile Glu Gly Gln Leu Val Gly Gly Gly Tyr Ala
 1               5                  10                  15

Ile Ser Pro Arg Thr Leu Val Ala Tyr Leu Arg Gly
            20                  25
```

<210> SEQ ID NO 6
<211> LENGTH: 28
<212> TYPE: PRT
<213> ORGANISM: Artificial Sequence
<220> FEATURE:
<223> OTHER INFORMATION: Description of Artificial Sequence: HIV PEPTIDE
<220> FEATURE:
<221> NAME/KEY: Variant
<222> LOCATION: 1
<223> OTHER INFORMATION: Phe
<220> FEATURE:
<221> NAME/KEY: Variant
<222> LOCATION: 2
<223> OTHER INFORMATION: Ile
<220> FEATURE:
<221> NAME/KEY: Variant
<222> LOCATION: 3
<223> OTHER INFORMATION: Leu
<220> FEATURE:
<221> NAME/KEY: Variant
<222> LOCATION: 4
<223> OTHER INFORMATION: Gln
<220> FEATURE:
<221> NAME/KEY: Variant -continued
<222> LOCATION: 5
<223> OTHER INFORMATION: Asn
<220> FEATURE:
<221> NAME/KEY: Variant
<222> LOCATION: 6
<223> OTHER INFORMATION: Ile
<220> FEATURE:
<221> NAME/KEY: Variant
<222> LOCATION: 7
<223> OTHER INFORMATION: Glu
<220> FEATURE:
<221> NAME/KEY: Variant
<222> LOCATION: 8
<223> OTHER INFORMATION: Gly
<220> FEATURE:
<221> NAME/KEY: Variant
<222> LOCATION: 9
<223> OTHER INFORMATION: Gln
<220> FEATURE:
<221> NAME/KEY: Variant
<222> LOCATION: 10
<223> OTHER INFORMATION: Leu
<220> FEATURE:
<221> NAME/KEY: Variant
<222> LOCATION: 11
<223> OTHER INFORMATION: Val
<220> FEATURE:
<221> NAME/KEY: Variant
<222> LOCATION: 12
<223> OTHER INFORMATION: Gly
<220> FEATURE:
<221> NAME/KEY: Variant
<222> LOCATION: 13
<223> OTHER INFORMATION: Gly
<220> FEATURE:
<221> NAME/KEY: Variant
<222> LOCATION: 14
<223> OTHER INFORMATION: Gly
<220> FEATURE:
<221> NAME/KEY: Variant
<222> LOCATION: 15
<223> OTHER INFORMATION: Tyr
<220> FEATURE:
<221> NAME/KEY: Variant
<222> LOCATION: 16
<223> OTHER INFORMATION: Ala
<220> FEATURE:
<221> NAME/KEY: Variant
<222> LOCATION: 17
<223> OTHER INFORMATION: Ile
<220> FEATURE:
<221> NAME/KEY: Variant
<222> LOCATION: 18
<223> OTHER INFORMATION: Ser
<220> FEATURE:
<221> NAME/KEY: Variant
<222> LOCATION: 19
<223> OTHER INFORMATION: Pro
<220> FEATURE:
<221> NAME/KEY: Variant
<222> LOCATION: 20
<223> OTHER INFORMATION: Arg
<220> FEATURE:
<221> NAME/KEY: Variant
<222> LOCATION: 21
<223> OTHER INFORMATION: Thr
<220> FEATURE:
<221> NAME/KEY: Variant
<222> LOCATION: 22
<223> OTHER INFORMATION: Leu
<220> FEATURE:
<221> NAME/KEY: Variant
<222> LOCATION: 23
<223> OTHER INFORMATION: Val
<220> FEATURE:
<221> NAME/KEY: Variant
<222> LOCATION: 24
<223> OTHER INFORMATION: Ala
<220> FEATURE:

-continued

<221> NAME/KEY: Variant
<222> LOCATION: 25
<223> OTHER INFORMATION: Gly
<220> FEATURE:
<221> NAME/KEY: Variant
<222> LOCATION: 26
<223> OTHER INFORMATION: Gly
<220> FEATURE:
<221> NAME/KEY: Variant
<222> LOCATION: 27
<223> OTHER INFORMATION: Gly
<220> FEATURE:
<221> NAME/KEY: Variant
<222> LOCATION: 28
<223> OTHER INFORMATION: Gly

<400> SEQUENCE: 6

```
Phe Ile Leu Gln Asn Ile Glu Gly Gln Leu Val Gly Gly Gly Tyr Ala
  1               5                  10                  15

Ile Ser Pro Arg Thr Leu Val Ala Gly Gly Gly Gly
             20                  25
```

<210> SEQ ID NO 7
<211> LENGTH: 26
<212> TYPE: PRT
<213> ORGANISM: Artificial Sequence
<220> FEATURE:
<223> OTHER INFORMATION: Description of Artificial Sequence: HIV PEPTIDE
<220> FEATURE:
<221> NAME/KEY: Variant
<222> LOCATION: 1
<223> OTHER INFORMATION: Pro
<220> FEATURE:
<221> NAME/KEY: Variant
<222> LOCATION: 2
<223> OTHER INFORMATION: Ile
<220> FEATURE:
<221> NAME/KEY: Variant
<222> LOCATION: 3
<223> OTHER INFORMATION: Val
<220> FEATURE:
<221> NAME/KEY: Variant
<222> LOCATION: 4
<223> OTHER INFORMATION: Gln
<220> FEATURE:
<221> NAME/KEY: Variant
<222> LOCATION: 5
<223> OTHER INFORMATION: Asn
<220> FEATURE:
<221> NAME/KEY: Variant
<222> LOCATION: 6
<223> OTHER INFORMATION: Ile
<220> FEATURE:
<221> NAME/KEY: Variant
<222> LOCATION: 7
<223> OTHER INFORMATION: Glu
<220> FEATURE:
<221> NAME/KEY: Variant
<222> LOCATION: 8
<223> OTHER INFORMATION: Gly
<220> FEATURE:
<221> NAME/KEY: Variant
<222> LOCATION: 9
<223> OTHER INFORMATION: Gln
<220> FEATURE:
<221> NAME/KEY: Variant
<222> LOCATION: 10
<223> OTHER INFORMATION: Met
<220> FEATURE:
<221> NAME/KEY: Variant
<222> LOCATION: 11
<223> OTHER INFORMATION: Val
<220> FEATURE:
<221> NAME/KEY: Variant
<222> LOCATION: 12
<223> OTHER INFORMATION: His -continued
<220> FEATURE:
<221> NAME/KEY: Variant
<222> LOCATION: 13
<223> OTHER INFORMATION: Gln
<220> FEATURE:
<221> NAME/KEY: Variant
<222> LOCATION: 14
<223> OTHER INFORMATION: Ala
<220> FEATURE:
<221> NAME/KEY: Variant
<222> LOCATION: 15
<223> OTHER INFORMATION: Ile
<220> FEATURE:
<221> NAME/KEY: Variant
<222> LOCATION: 16
<223> OTHER INFORMATION: Ser
<220> FEATURE:
<221> NAME/KEY: Variant
<222> LOCATION: 17
<223> OTHER INFORMATION: Pro
<220> FEATURE:
<221> NAME/KEY: Variant
<222> LOCATION: 18
<223> OTHER INFORMATION: Arg
<220> FEATURE:
<221> NAME/KEY: Variant
<222> LOCATION: 19
<223> OTHER INFORMATION: Thr
<220> FEATURE:
<221> NAME/KEY: Variant
<222> LOCATION: 20
<223> OTHER INFORMATION: Leu
<220> FEATURE:
<221> NAME/KEY: Variant
<222> LOCATION: 21
<223> OTHER INFORMATION: Asn
<220> FEATURE:
<221> NAME/KEY: Variant
<222> LOCATION: 22
<223> OTHER INFORMATION: Ala
<220> FEATURE:
<221> NAME/KEY: Variant
<222> LOCATION: 23
<223> OTHER INFORMATION: Trp
<220> FEATURE:
<221> NAME/KEY: Variant
<222> LOCATION: 24
<223> OTHER INFORMATION: Val
<220> FEATURE:
<221> NAME/KEY: Variant
<222> LOCATION: 25
<223> OTHER INFORMATION: Lys
<220> FEATURE:
<221> NAME/KEY: Variant
<222> LOCATION: 26
<223> OTHER INFORMATION: Val

<400> SEQUENCE: 7

```
Pro Ile Val Gln Asn Ile Glu Gly Gln Met Val His Gln Ala Ile Ser
  1               5                  10                  15

Pro Arg Thr Leu Asn Ala Trp Val Lys Val
             20                  25
```

<210> SEQ ID NO 8
<211> LENGTH: 25
<212> TYPE: PRT
<213> ORGANISM: Artificial Sequence
<220> FEATURE:
<223> OTHER INFORMATION: Description of Artificial Sequence: HIV PEPTIDE
<220> FEATURE:
<221> NAME/KEY: Variant
<222> LOCATION: 1
<223> OTHER INFORMATION: Phe
<220> FEATURE:
<221> NAME/KEY: Variant
<222> LOCATION: 2

-continued

<223> OTHER INFORMATION: Ile
<220> FEATURE:
<221> NAME/KEY: Variant
<222> LOCATION: 3
<223> OTHER INFORMATION: Leu
<220> FEATURE:
<221> NAME/KEY: Variant
<222> LOCATION: 4
<223> OTHER INFORMATION: Gln
<220> FEATURE:
<221> NAME/KEY: Variant
<222> LOCATION: 5
<223> OTHER INFORMATION: Asn
<220> FEATURE:
<221> NAME/KEY: Variant
<222> LOCATION: 6
<223> OTHER INFORMATION: Ile
<220> FEATURE:
<221> NAME/KEY: Variant
<222> LOCATION: 7
<223> OTHER INFORMATION: Gln
<220> FEATURE:
<221> NAME/KEY: Variant
<222> LOCATION: 8
<223> OTHER INFORMATION: Gly
<220> FEATURE:
<221> NAME/KEY: Variant
<222> LOCATION: 9
<223> OTHER INFORMATION: Gln
<220> FEATURE:
<221> NAME/KEY: Variant
<222> LOCATION: 10
<223> OTHER INFORMATION: Leu
<220> FEATURE:
<221> NAME/KEY: Variant
<222> LOCATION: 11
<223> OTHER INFORMATION: Val
<220> FEATURE:
<221> NAME/KEY: Variant
<222> LOCATION: 12
<223> OTHER INFORMATION: Gly
<220> FEATURE:
<221> NAME/KEY: Variant
<222> LOCATION: 13
<223> OTHER INFORMATION: Gly
<220> FEATURE:
<221> NAME/KEY: Variant
<222> LOCATION: 14
<223> OTHER INFORMATION: Gly
<220> FEATURE:
<221> NAME/KEY: Variant
<222> LOCATION: 15
<223> OTHER INFORMATION: Tyr
<220> FEATURE:
<221> NAME/KEY: Variant
<222> LOCATION: 16
<223> OTHER INFORMATION: Ala
<220> FEATURE:
<221> NAME/KEY: Variant
<222> LOCATION: 17
<223> OTHER INFORMATION: Ile
<220> FEATURE:
<221> NAME/KEY: Variant
<222> LOCATION: 18
<223> OTHER INFORMATION: Ser
<220> FEATURE:
<221> NAME/KEY: Variant
<222> LOCATION: 19
<223> OTHER INFORMATION: Pro
<220> FEATURE:
<221> NAME/KEY: Variant
<222> LOCATION: 20
<223> OTHER INFORMATION: Arg
<220> FEATURE:
<221> NAME/KEY: Variant
<222> LOCATION: 21
<223> OTHER INFORMATION: Thr
<220> FEATURE:
<221> NAME/KEY: Variant -continued
<222> LOCATION: 22
<223> OTHER INFORMATION: Leu
<220> FEATURE:
<221> NAME/KEY: Variant
<222> LOCATION: 23
<223> OTHER INFORMATION: Val
<220> FEATURE:
<221> NAME/KEY: Variant
<222> LOCATION: 24
<223> OTHER INFORMATION: Ala
<220> FEATURE:
<221> NAME/KEY: Variant
<222> LOCATION: 25
<223> OTHER INFORMATION: Gly

<400> SEQUENCE: 8

```
Phe Ile Leu Gln Asn Ile Gln Gly Gln Leu Val Gly Gly Gly Tyr Ala
  1               5                  10                  15
Ile Ser Pro Arg Thr Leu Val Ala Gly
             20                  25
```

<210> SEQ ID NO 9
<211> LENGTH: 25
<212> TYPE: PRT
<213> ORGANISM: Artificial Sequence
<220> FEATURE:
<223> OTHER INFORMATION: Description of Artificial Sequence: HIV PEPTIDE
<220> FEATURE:
<221> NAME/KEY: 1
<222> LOCATION: Variant
<223> OTHER INFORMATION: Tyr Trp Phe or Gly
<220> FEATURE:
<221> NAME/KEY: Variant
<222> LOCATION: 2
<223> OTHER INFORMATION: Ala
<220> FEATURE:
<221> NAME/KEY: 3
<222> LOCATION: Variant
<223> OTHER INFORMATION: Thr Ala Val Ile or Leu
<220> FEATURE:
<221> NAME/KEY: 4
<222> LOCATION: Variant
<223> OTHER INFORMATION: Pro or Ser
<220> FEATURE:
<221> NAME/KEY: 5
<222> LOCATION: Variant
<223> OTHER INFORMATION: Gln His Gly Thr Ser or Tyr
<220> FEATURE:
<221> NAME/KEY: Variant
<222> LOCATION: 6
<223> OTHER INFORMATION: Ala
<220> FEATURE:
<221> NAME/KEY: Variant
<222> LOCATION: 7
<223> OTHER INFORMATION: Leu Ile or Val
<220> FEATURE:
<221> NAME/KEY: Variant
<222> LOCATION: 8
<223> OTHER INFORMATION: Asn or Tyr
<220> FEATURE:
<221> NAME/KEY: Variant
<222> LOCATION: 9
<223> OTHER INFORMATION: Thr Met Leu or Ala
<220> FEATURE:
<221> NAME/KEY: Variant
<222> LOCATION: 10
<223> OTHER INFORMATION: Leu
<220> FEATURE:
<221> NAME/KEY: Variant
<222> LOCATION: 11
<223> OTHER INFORMATION: Leu
<220> FEATURE:
<221> NAME/KEY: Variant
<222> LOCATION: 12
<223> OTHER INFORMATION: Ser Thr or Asn
<220> FEATURE:
<221> NAME/KEY: Variant -continued
<222> LOCATION: 13
<223> OTHER INFORMATION: Thr Ile Val or Ala
<220> FEATURE:
<221> NAME/KEY: Variant
<222> LOCATION: 14
<223> OTHER INFORMATION: Val or Ile
<220> FEATURE:
<221> NAME/KEY: Variant
<222> LOCATION: 15
<223> OTHER INFORMATION: Gly or none or PEG Linker
<220> FEATURE:
<221> NAME/KEY: Variant
<222> LOCATION: 16
<223> OTHER INFORMATION: Gly or none or PEG Linker
<220> FEATURE:
<221> NAME/KEY: Variant
<222> LOCATION: 17
<223> OTHER INFORMATION: Gly or none or PEG Linker
<220> FEATURE:
<221> NAME/KEY: Variant
<222> LOCATION: 18
<223> OTHER INFORMATION: Gly or None
<220> FEATURE:
<221> NAME/KEY: Variant
<222> LOCATION: 19
<223> OTHER INFORMATION: Gly or none
<220> FEATURE:
<221> NAME/KEY: Variant
<222> LOCATION: 20
<223> OTHER INFORMATION: His
<220> FEATURE:
<221> NAME/KEY: Variant
<222> LOCATION: 21
<223> OTHER INFORMATION: Gln
<220> FEATURE:
<221> NAME/KEY: Variant
<222> LOCATION: 22
<223> OTHER INFORMATION: Ala or Gly
<220> FEATURE:
<221> NAME/KEY: Variant
<222> LOCATION: 23
<223> OTHER INFORMATION: Ala
<220> FEATURE:
<221> NAME/KEY: Variant
<222> LOCATION: 24
<223> OTHER INFORMATION: Met Leu Cys or none
<220> FEATURE:
<221> NAME/KEY: Variant
<222> LOCATION: 25
<223> OTHER INFORMATION: Gln Glu His Gly or none

<400> SEQUENCE: 9

```
Xaa Ala Xaa Xaa Xaa Ala Xaa Xaa Xaa Leu Leu Xaa Xaa Xaa Xaa Xaa
  1               5                  10                  15

Xaa Xaa Xaa His Gln Xaa Ala Xaa Xaa
             20                  25
```

<210> SEQ ID NO 10
<211> LENGTH: 20
<212> TYPE: PRT
<213> ORGANISM: Artificial Sequence
<220> FEATURE:
<223> OTHER INFORMATION: Description of Artificial Sequence: HIV PEPTIDE
<220> FEATURE:
<221> NAME/KEY: Variant
<222> LOCATION: 1
<223> OTHER INFORMATION: Gly
<220> FEATURE:
<221> NAME/KEY: Variant
<222> LOCATION: 2
<223> OTHER INFORMATION: Ala
<220> FEATURE:
<221> NAME/KEY: Variant
<222> LOCATION: 3
<223> OTHER INFORMATION: Thr
<220> FEATURE:

-continued

<221> NAME/KEY: Variant
<222> LOCATION: 4
<223> OTHER INFORMATION: Pro
<220> FEATURE:
<221> NAME/KEY: Variant
<222> LOCATION: 5
<223> OTHER INFORMATION: Gln
<220> FEATURE:
<221> NAME/KEY: Variant
<222> LOCATION: 6
<223> OTHER INFORMATION: Asp
<220> FEATURE:
<221> NAME/KEY: Variant
<222> LOCATION: 7
<223> OTHER INFORMATION: Leu
<220> FEATURE:
<221> NAME/KEY: Variant
<222> LOCATION: 8
<223> OTHER INFORMATION: Asn
<220> FEATURE:
<221> NAME/KEY: Variant
<222> LOCATION: 9
<223> OTHER INFORMATION: Thr
<220> FEATURE:
<221> NAME/KEY: Variant
<222> LOCATION: 10
<223> OTHER INFORMATION: Met
<220> FEATURE:
<221> NAME/KEY: Variant
<222> LOCATION: 11
<223> OTHER INFORMATION: Leu
<220> FEATURE:
<221> NAME/KEY: Variant
<222> LOCATION: 12
<223> OTHER INFORMATION: Asn
<220> FEATURE:
<221> NAME/KEY: Variant
<222> LOCATION: 13
<223> OTHER INFORMATION: Thr
<220> FEATURE:
<221> NAME/KEY: Variant
<222> LOCATION: 14
<223> OTHER INFORMATION: Val
<220> FEATURE:
<221> NAME/KEY: Variant
<222> LOCATION: 15
<223> OTHER INFORMATION: Gly
<220> FEATURE:
<221> NAME/KEY: Variant
<222> LOCATION: 16
<223> OTHER INFORMATION: Gly
<220> FEATURE:
<221> NAME/KEY: Variant
<222> LOCATION: 17
<223> OTHER INFORMATION: His
<220> FEATURE:
<221> NAME/KEY: Variant
<222> LOCATION: 18
<223> OTHER INFORMATION: Gln
<220> FEATURE:
<221> NAME/KEY: Variant
<222> LOCATION: 19
<223> OTHER INFORMATION: Ala
<220> FEATURE:
<221> NAME/KEY: Variant
<222> LOCATION: 20
<223> OTHER INFORMATION: Ala

<400> SEQUENCE: 10

```
Gly Ala Thr Pro Gln Asp Leu Asn Thr Met Leu Asn Thr Val Gly Gly
  1               5                  10                  15

His Gln Ala Ala
             20
```

<210> SEQ ID NO 11
<211> LENGTH: 20

-continued

<212> TYPE: PRT
<213> ORGANISM: Artificial Sequence
<220> FEATURE:
<223> OTHER INFORMATION: Description of Artificial Sequence: HIV PEPTIDE
<220> FEATURE:
<221> NAME/KEY: Variant
<222> LOCATION: 1
<223> OTHER INFORMATION: Tyr
<220> FEATURE:
<221> NAME/KEY: Variant
<222> LOCATION: 2
<223> OTHER INFORMATION: Ala
<220> FEATURE:
<221> NAME/KEY: Variant
<222> LOCATION: 3
<223> OTHER INFORMATION: Ile
<220> FEATURE:
<221> NAME/KEY: Variant
<222> LOCATION: 4
<223> OTHER INFORMATION: Pro
<220> FEATURE:
<221> NAME/KEY: Variant
<222> LOCATION: 5
<223> OTHER INFORMATION: Gln
<220> FEATURE:
<221> NAME/KEY: Variant
<222> LOCATION: 6
<223> OTHER INFORMATION: Ala
<220> FEATURE:
<221> NAME/KEY: Variant
<222> LOCATION: 7
<223> OTHER INFORMATION: Leu
<220> FEATURE:
<221> NAME/KEY: Variant
<222> LOCATION: 8
<223> OTHER INFORMATION: Asn
<220> FEATURE:
<221> NAME/KEY: Variant
<222> LOCATION: 9
<223> OTHER INFORMATION: Thr
<220> FEATURE:
<221> NAME/KEY: Variant
<222> LOCATION: 10
<223> OTHER INFORMATION: Leu
<220> FEATURE:
<221> NAME/KEY: Variant
<222> LOCATION: 11
<223> OTHER INFORMATION: Leu
<220> FEATURE:
<221> NAME/KEY: Variant
<222> LOCATION: 12
<223> OTHER INFORMATION: Asn
<220> FEATURE:
<221> NAME/KEY: Variant
<222> LOCATION: 13
<223> OTHER INFORMATION: Thr
<220> FEATURE:
<221> NAME/KEY: Variant
<222> LOCATION: 14
<223> OTHER INFORMATION: Val
<220> FEATURE:
<221> NAME/KEY: Variant
<222> LOCATION: 15
<223> OTHER INFORMATION: Gly
<220> FEATURE:
<221> NAME/KEY: Variant
<222> LOCATION: 16
<223> OTHER INFORMATION: Gly
<220> FEATURE:
<221> NAME/KEY: Variant
<222> LOCATION: 17
<223> OTHER INFORMATION: His
<220> FEATURE:
<221> NAME/KEY: Variant
<222> LOCATION: 18
<223> OTHER INFORMATION: Gln
<220> FEATURE:
<221> NAME/KEY: Variant
<222> LOCATION: 19

-continued

<223> OTHER INFORMATION: Ala
<220> FEATURE:
<221> NAME/KEY: Variant
<222> LOCATION: 20
<223> OTHER INFORMATION: Ala

<400> SEQUENCE: 11

Tyr Ala Ile Pro Gln Ala Leu Asn Thr Leu Leu Asn Thr Val Gly Gly
1 5 10 15

His Gln Ala Ala
20

<210> SEQ ID NO 12
<211> LENGTH: 24
<212> TYPE: PRT
<213> ORGANISM: Artificial Sequence
<220> FEATURE:
<223> OTHER INFORMATION: Description of Artificial Sequence: HIV PEPTIDE
<220> FEATURE:
<221> NAME/KEY: Variant
<222> LOCATION: 1
<223> OTHER INFORMATION: Phe
<220> FEATURE:
<221> NAME/KEY: Variant
<222> LOCATION: 2
<223> OTHER INFORMATION: Ala
<220> FEATURE:
<221> NAME/KEY: Variant
<222> LOCATION: 3
<223> OTHER INFORMATION: Ile
<220> FEATURE:
<221> NAME/KEY: Variant
<222> LOCATION: 4
<223> OTHER INFORMATION: Pro
<220> FEATURE:
<221> NAME/KEY: Variant
<222> LOCATION: 5
<223> OTHER INFORMATION: Gln
<220> FEATURE:
<221> NAME/KEY: Variant
<222> LOCATION: 6
<223> OTHER INFORMATION: Ala
<220> FEATURE:
<221> NAME/KEY: Variant
<222> LOCATION: 7
<223> OTHER INFORMATION: Leu
<220> FEATURE:
<221> NAME/KEY: Variant
<222> LOCATION: 8
<223> OTHER INFORMATION: Asn
<220> FEATURE:
<221> NAME/KEY: Variant
<222> LOCATION: 9
<223> OTHER INFORMATION: Thr
<220> FEATURE:
<221> NAME/KEY: Variant
<222> LOCATION: 10
<223> OTHER INFORMATION: Leu
<220> FEATURE:
<221> NAME/KEY: Variant
<222> LOCATION: 11
<223> OTHER INFORMATION: Leu
<220> FEATURE:
<221> NAME/KEY: Variant
<222> LOCATION: 12
<223> OTHER INFORMATION: Asn
<220> FEATURE:
<221> NAME/KEY: Variant
<222> LOCATION: 13
<223> OTHER INFORMATION: Thr
<220> FEATURE:
<221> NAME/KEY: Variant
<222> LOCATION: 14
<223> OTHER INFORMATION: Val
<220> FEATURE:
<221> NAME/KEY: Variant -continued
<222> LOCATION: 15
<223> OTHER INFORMATION: Gly
<220> FEATURE:
<221> NAME/KEY: Variant
<222> LOCATION: 16
<223> OTHER INFORMATION: Gly
<220> FEATURE:
<221> NAME/KEY: Variant
<222> LOCATION: 17
<223> OTHER INFORMATION: Gly
<220> FEATURE:
<221> NAME/KEY: Variant
<222> LOCATION: 18
<223> OTHER INFORMATION: Gly
<220> FEATURE:
<221> NAME/KEY: Variant
<222> LOCATION: 19
<223> OTHER INFORMATION: His
<220> FEATURE:
<221> NAME/KEY: Variant
<222> LOCATION: 20
<223> OTHER INFORMATION: Gln
<220> FEATURE:
<221> NAME/KEY: Variant
<222> LOCATION: 21
<223> OTHER INFORMATION: Ala
<220> FEATURE:
<221> NAME/KEY: Variant
<222> LOCATION: 22
<223> OTHER INFORMATION: Ala
<220> FEATURE:
<221> NAME/KEY: Variant
<222> LOCATION: 23
<223> OTHER INFORMATION: Cys
<220> FEATURE:
<221> NAME/KEY: Variant
<222> LOCATION: 24
<223> OTHER INFORMATION: Gly

<400> SEQUENCE: 12

```
Phe Ala Ile Pro Gln Ala Leu Asn Thr Leu Leu Asn Thr Val Gly Gly
  1               5                  10                  15

Gly Gly His Gln Ala Ala Cys Gly
             20
```

<210> SEQ ID NO 13
<211> LENGTH: 19
<212> TYPE: PRT
<213> ORGANISM: Artificial Sequence
<220> FEATURE:
<223> OTHER INFORMATION: Description of Artificial Sequence: HIV PEPTIDE
<220> FEATURE:
<221> NAME/KEY: Variant
<222> LOCATION: 1
<223> OTHER INFORMATION: Gly
<220> FEATURE:
<221> NAME/KEY: Variant
<222> LOCATION: 2
<223> OTHER INFORMATION: Ser
<220> FEATURE:
<221> NAME/KEY: Variant
<222> LOCATION: 3
<223> OTHER INFORMATION: Asp
<220> FEATURE:
<221> NAME/KEY: Variant
<222> LOCATION: 4
<223> OTHER INFORMATION: Ile
<220> FEATURE:
<221> NAME/KEY: Variant
<222> LOCATION: 5
<223> OTHER INFORMATION: Ala
<220> FEATURE:
<221> NAME/KEY: Variant
<222> LOCATION: 6
<223> OTHER INFORMATION: Gly
<220> FEATURE:

-continued

```
<221> NAME/KEY: Variant
<222> LOCATION: 7
<223> OTHER INFORMATION: Thr
<220> FEATURE:
<221> NAME/KEY: Variant
<222> LOCATION: 8
<223> OTHER INFORMATION: Thr
<220> FEATURE:
<221> NAME/KEY: Variant
<222> LOCATION: 9
<223> OTHER INFORMATION: Ser
<220> FEATURE:
<221> NAME/KEY: Variant
<222> LOCATION: 10
<223> OTHER INFORMATION: Thr
<220> FEATURE:
<221> NAME/KEY: Variant
<222> LOCATION: 11
<223> OTHER INFORMATION: Leu
<220> FEATURE:
<221> NAME/KEY: Variant
<222> LOCATION: 12
<223> OTHER INFORMATION: Gln
<220> FEATURE:
<221> NAME/KEY: Variant
<222> LOCATION: 13
<223> OTHER INFORMATION: Glu
<220> FEATURE:
<221> NAME/KEY: Variant
<222> LOCATION: 14
<223> OTHER INFORMATION: Gln
<220> FEATURE:
<221> NAME/KEY: Variant
<222> LOCATION: 15
<223> OTHER INFORMATION: Ile
<220> FEATURE:
<221> NAME/KEY: Variant
<222> LOCATION: 16
<223> OTHER INFORMATION: Gly
<220> FEATURE:
<221> NAME/KEY: Variant
<222> LOCATION: 17
<223> OTHER INFORMATION: Trp
<220> FEATURE:
<221> NAME/KEY: Variant
<222> LOCATION: 18
<223> OTHER INFORMATION: Met
<220> FEATURE:
<221> NAME/KEY: Variant
<222> LOCATION: 19
<223> OTHER INFORMATION: Thr

<400> SEQUENCE: 13

Gly Ser Asp Ile Ala Gly Thr Thr Ser Thr Leu Gln Glu Gln Ile Gly
  1               5                  10                  15

Trp Met Thr


<210> SEQ ID NO 14
<211> LENGTH: 19
<212> TYPE: PRT
<213> ORGANISM: Artificial Sequence
<220> FEATURE:
<223> OTHER INFORMATION: Description of Artificial Sequence: HIV PEPTIDE
<220> FEATURE:
<221> NAME/KEY: Variant
<222> LOCATION: 1
<223> OTHER INFORMATION: Trp
<220> FEATURE:
<221> NAME/KEY: Variant
<222> LOCATION: 2
<223> OTHER INFORMATION: Ser
<220> FEATURE:
<221> NAME/KEY: Variant
<222> LOCATION: 3
<223> OTHER INFORMATION: Ala
<220> FEATURE:
```

-continued

<221> NAME/KEY: Variant
<222> LOCATION: 4
<223> OTHER INFORMATION: Leu
<220> FEATURE:
<221> NAME/KEY: Variant
<222> LOCATION: 5
<223> OTHER INFORMATION: Ala
<220> FEATURE:
<221> NAME/KEY: Variant
<222> LOCATION: 6
<223> OTHER INFORMATION: Gly
<220> FEATURE:
<221> NAME/KEY: Variant
<222> LOCATION: 7
<223> OTHER INFORMATION: Thr
<220> FEATURE:
<221> NAME/KEY: Variant
<222> LOCATION: 8
<223> OTHER INFORMATION: Thr
<220> FEATURE:
<221> NAME/KEY: Variant
<222> LOCATION: 9
<223> OTHER INFORMATION: Ser
<220> FEATURE:
<221> NAME/KEY: Variant
<222> LOCATION: 10
<223> OTHER INFORMATION: Leu
<220> FEATURE:
<221> NAME/KEY: Variant
<222> LOCATION: 11
<223> OTHER INFORMATION: Leu
<220> FEATURE:
<221> NAME/KEY: Variant
<222> LOCATION: 12
<223> OTHER INFORMATION: Gln
<220> FEATURE:
<221> NAME/KEY: Variant
<222> LOCATION: 13
<223> OTHER INFORMATION: Gly
<220> FEATURE:
<221> NAME/KEY: Variant
<222> LOCATION: 14
<223> OTHER INFORMATION: Gln
<220> FEATURE:
<221> NAME/KEY: Variant
<222> LOCATION: 15
<223> OTHER INFORMATION: Leu
<220> FEATURE:
<221> NAME/KEY: Variant
<222> LOCATION: 16
<223> OTHER INFORMATION: Gly
<220> FEATURE:
<221> NAME/KEY: Variant
<222> LOCATION: 17
<223> OTHER INFORMATION: Trp
<220> FEATURE:
<221> NAME/KEY: Variant
<222> LOCATION: 18
<223> OTHER INFORMATION: Ile
<220> FEATURE:
<221> NAME/KEY: Variant
<222> LOCATION: 19
<223> OTHER INFORMATION: Thr

<400> SEQUENCE: 14

```
Trp Ser Ala Leu Ala Gly Thr Thr Ser Leu Leu Gln Gly Gln Leu Gly
  1               5                  10                  15

Trp Ile Thr
```

<210> SEQ ID NO 15
<211> LENGTH: 21
<212> TYPE: PRT
<213> ORGANISM: Artificial Sequence
<220> FEATURE:
<223> OTHER INFORMATION: Description of Artificial Sequence: HIV PEPTIDE
<220> FEATURE:

-continued

<221> NAME/KEY: 1
<222> LOCATION: Variant
<223> OTHER INFORMATION: Trp or Tyr
<220> FEATURE:
<221> NAME/KEY: 2
<222> LOCATION: Variant
<223> OTHER INFORMATION: Ser or Ala
<220> FEATURE:
<221> NAME/KEY: Variant
<222> LOCATION: 3
<223> OTHER INFORMATION: Ala
<220> FEATURE:
<221> NAME/KEY: Variant
<222> LOCATION: 4
<223> OTHER INFORMATION: Leu
<220> FEATURE:
<221> NAME/KEY: Variant
<222> LOCATION: 5
<223> OTHER INFORMATION: Ala
<220> FEATURE:
<221> NAME/KEY: Variant
<222> LOCATION: 6
<223> OTHER INFORMATION: Gly
<220> FEATURE:
<221> NAME/KEY: Variant
<222> LOCATION: 7
<223> OTHER INFORMATION: Thr Ala or Ser
<220> FEATURE:
<221> NAME/KEY: Variant
<222> LOCATION: 8
<223> OTHER INFORMATION: Ser or Thr
<220> FEATURE:
<221> NAME/KEY: Variant
<222> LOCATION: 9
<223> OTHER INFORMATION: Ser or Thr
<220> FEATURE:
<221> NAME/KEY: Variant
<222> LOCATION: 10
<223> OTHER INFORMATION: Leu
<220> FEATURE:
<221> NAME/KEY: Variant
<222> LOCATION: 11
<223> OTHER INFORMATION: Leu Pro Val or Gln
<220> FEATURE:
<221> NAME/KEY: Variant
<222> LOCATION: 12
<223> OTHER INFORMATION: Gln Ala or His
<220> FEATURE:
<221> NAME/KEY: Variant
<222> LOCATION: 13
<223> OTHER INFORMATION: Gly or Glu
<220> FEATURE:
<221> NAME/KEY: Variant
<222> LOCATION: 14
<223> OTHER INFORMATION: Gln or His
<220> FEATURE:
<221> NAME/KEY: Variant
<222> LOCATION: 15
<223> OTHER INFORMATION: Ile Leu Val or Met
<220> FEATURE:
<221> NAME/KEY: Variant
<222> LOCATION: 16
<223> OTHER INFORMATION: Gly Ala Gln Thr Asn Arg His or Ile
<220> FEATURE:
<221> NAME/KEY: Variant
<222> LOCATION: 17
<223> OTHER INFORMATION: Trp or Tyr
<220> FEATURE:
<221> NAME/KEY: Variant
<222> LOCATION: 18
<223> OTHER INFORMATION: Thr Ile Leu or Met
<220> FEATURE:
<221> NAME/KEY: Variant
<222> LOCATION: 19
<223> OTHER INFORMATION: Thr or Ser
<220> FEATURE:
<221> NAME/KEY: Variant
<222> LOCATION: 20
<223> OTHER INFORMATION: Cys Gly or None -continued
<220> FEATURE:
<221> NAME/KEY: Variant
<222> LOCATION: 21
<223> OTHER INFORMATION: Gly or none

<400> SEQUENCE: 15

Xaa Xaa Ala Leu Ala Gly Xaa Xaa Xaa Leu Xaa Xaa Xaa Xaa Xaa Xaa
1 5 10 15

Xaa Xaa Xaa Xaa Xaa
20

<210> SEQ ID NO 16
<211> LENGTH: 21
<212> TYPE: PRT
<213> ORGANISM: Artificial Sequence
<220> FEATURE:
<223> OTHER INFORMATION: Description of Artificial Sequence: HIV PEPTIDE
<220> FEATURE:
<221> NAME/KEY: Variant
<222> LOCATION: 1
<223> OTHER INFORMATION: His
<220> FEATURE:
<221> NAME/KEY: Variant
<222> LOCATION: 2
<223> OTHER INFORMATION: Ile
<220> FEATURE:
<221> NAME/KEY: Variant
<222> LOCATION: 3
<223> OTHER INFORMATION: Val
<220> FEATURE:
<221> NAME/KEY: Variant
<222> LOCATION: 4
<223> OTHER INFORMATION: Trp
<220> FEATURE:
<221> NAME/KEY: Variant
<222> LOCATION: 5
<223> OTHER INFORMATION: Ala
<220> FEATURE:
<221> NAME/KEY: Variant
<222> LOCATION: 6
<223> OTHER INFORMATION: Ser
<220> FEATURE:
<221> NAME/KEY: Variant
<222> LOCATION: 7
<223> OTHER INFORMATION: Arg
<220> FEATURE:
<221> NAME/KEY: Variant
<222> LOCATION: 8
<223> OTHER INFORMATION: Glu
<220> FEATURE:
<221> NAME/KEY: Variant
<222> LOCATION: 9
<223> OTHER INFORMATION: Leu
<220> FEATURE:
<221> NAME/KEY: Variant
<222> LOCATION: 10
<223> OTHER INFORMATION: Glu
<220> FEATURE:
<221> NAME/KEY: Variant
<222> LOCATION: 11
<223> OTHER INFORMATION: Arg
<220> FEATURE:
<221> NAME/KEY: Variant
<222> LOCATION: 12
<223> OTHER INFORMATION: Phe
<220> FEATURE:
<221> NAME/KEY: Variant
<222> LOCATION: 13
<223> OTHER INFORMATION: Ala
<220> FEATURE:
<221> NAME/KEY: Variant
<222> LOCATION: 14
<223> OTHER INFORMATION: Val
<220> FEATURE:
<221> NAME/KEY: Variant
<222> LOCATION: 15

-continued

<223> OTHER INFORMATION: Asn
<220> FEATURE:
<221> NAME/KEY: Variant
<222> LOCATION: 16
<223> OTHER INFORMATION: Pro
<220> FEATURE:
<221> NAME/KEY: Variant
<222> LOCATION: 17
<223> OTHER INFORMATION: Gly
<220> FEATURE:
<221> NAME/KEY: Variant
<222> LOCATION: 18
<223> OTHER INFORMATION: Leu
<220> FEATURE:
<221> NAME/KEY: Variant
<222> LOCATION: 19
<223> OTHER INFORMATION: Leu
<220> FEATURE:
<221> NAME/KEY: Variant
<222> LOCATION: 20
<223> OTHER INFORMATION: Glu
<220> FEATURE:
<221> NAME/KEY: Variant
<222> LOCATION: 21
<223> OTHER INFORMATION: Thr

<400> SEQUENCE: 16

```
His Ile Val Trp Ala Ser Arg Glu Leu Glu Arg Phe Ala Val Asn Pro
  1               5                  10                  15

Gly Leu Leu Glu Thr
             20
```

<210> SEQ ID NO 17
<211> LENGTH: 23
<212> TYPE: PRT
<213> ORGANISM: Artificial Sequence
<220> FEATURE:
<223> OTHER INFORMATION: Description of Artificial Sequence: HIV PEPTIDE
<220> FEATURE:
<221> NAME/KEY: Variant
<222> LOCATION: 1
<223> OTHER INFORMATION: Pro
<220> FEATURE:
<221> NAME/KEY: Variant
<222> LOCATION: 2
<223> OTHER INFORMATION: Ile
<220> FEATURE:
<221> NAME/KEY: Variant
<222> LOCATION: 3
<223> OTHER INFORMATION: Val
<220> FEATURE:
<221> NAME/KEY: Variant
<222> LOCATION: 4
<223> OTHER INFORMATION: Gln
<220> FEATURE:
<221> NAME/KEY: Variant
<222> LOCATION: 5
<223> OTHER INFORMATION: Asn
<220> FEATURE:
<221> NAME/KEY: Variant
<222> LOCATION: 6
<223> OTHER INFORMATION: Ile
<220> FEATURE:
<221> NAME/KEY: Variant
<222> LOCATION: 7
<223> OTHER INFORMATION: Gln
<220> FEATURE:
<221> NAME/KEY: Variant
<222> LOCATION: 8
<223> OTHER INFORMATION: Gly
<220> FEATURE:
<221> NAME/KEY: Variant
<222> LOCATION: 9
<223> OTHER INFORMATION: Gln
<220> FEATURE:
<221> NAME/KEY: Variant -continued

```
<222> LOCATION: 10
<223> OTHER INFORMATION: Met
<220> FEATURE:
<221> NAME/KEY: Variant
<222> LOCATION: 11
<223> OTHER INFORMATION: Val
<220> FEATURE:
<221> NAME/KEY: Variant
<222> LOCATION: 12
<223> OTHER INFORMATION: His
<220> FEATURE:
<221> NAME/KEY: Variant
<222> LOCATION: 13
<223> OTHER INFORMATION: Gln
<220> FEATURE:
<221> NAME/KEY: Variant
<222> LOCATION: 14
<223> OTHER INFORMATION: Ala
<220> FEATURE:
<221> NAME/KEY: Variant
<222> LOCATION: 15
<223> OTHER INFORMATION: Ile
<220> FEATURE:
<221> NAME/KEY: Variant
<222> LOCATION: 16
<223> OTHER INFORMATION: Ser
<220> FEATURE:
<221> NAME/KEY: Variant
<222> LOCATION: 17
<223> OTHER INFORMATION: Pro
<220> FEATURE:
<221> NAME/KEY: Variant
<222> LOCATION: 18
<223> OTHER INFORMATION: Arg
<220> FEATURE:
<221> NAME/KEY: Variant
<222> LOCATION: 19
<223> OTHER INFORMATION: Thr
<220> FEATURE:
<221> NAME/KEY: Variant
<222> LOCATION: 20
<223> OTHER INFORMATION: Leu
<220> FEATURE:
<221> NAME/KEY: Variant
<222> LOCATION: 21
<223> OTHER INFORMATION: Asn
<220> FEATURE:
<221> NAME/KEY: Variant
<222> LOCATION: 22
<223> OTHER INFORMATION: Ala
<220> FEATURE:
<221> NAME/KEY: Variant
<222> LOCATION: 23
<223> OTHER INFORMATION: Trp

<400> SEQUENCE: 17

Pro Ile Val Gln Asn Ile Gln Gly Gln Met Val His Gln Ala Ile Ser
  1               5                  10                  15

Pro Arg Thr Leu Asn Ala Trp
            20
```